US008802394B2

(12) United States Patent
Minea et al.

(10) Patent No.: US 8,802,394 B2
(45) Date of Patent: Aug. 12, 2014

(54) METHOD OF EXPRESSING PROTEINS WITH DISULFIDE BRIDGES WITH ENHANCED YIELDS AND ACTIVITY

(76) Inventors: Radu O. Minea, Arcadia, CA (US); Stephen D. Swenson, Arcadia, CA (US); Francis S. Markland, Jr., Manhattan Beach, CA (US)

( * ) Notice: Subject to any disclaimer, the term of this patent is extended or adjusted under 35 U.S.C. 154(b) by 8 days.

(21) Appl. No.: 13/127,970

(22) PCT Filed: Nov. 12, 2009

(86) PCT No.: PCT/US2009/064256
§ 371 (c)(1),
(2), (4) Date: Jul. 28, 2011

(87) PCT Pub. No.: WO2010/056901
PCT Pub. Date: May 20, 2010

(65) Prior Publication Data
US 2011/0300579 A1 Dec. 8, 2011

Related U.S. Application Data

(60) Provisional application No. 61/114,435, filed on Nov. 13, 2008.

(51) Int. Cl.
*C12P 21/04* (2006.01)
*C12N 1/21* (2006.01)

(52) U.S. Cl.
USPC ..................... 435/69.1; 435/252.33

(58) Field of Classification Search
None
See application file for complete search history.

(56) References Cited

U.S. PATENT DOCUMENTS

| | | | |
|---|---|---|---|
| 4,610,879 A | 9/1986 | Markland et al. |
| 5,066,592 A | 11/1991 | Huang et al. |
| 5,227,400 A | 7/1993 | Holton et al. |
| 5,248,796 A | 9/1993 | Chen et al. |
| 5,250,683 A | 10/1993 | Holton et al. |
| 5,254,580 A | 10/1993 | Chen et al. |
| 5,272,171 A | 12/1993 | Ueda et al. |
| 5,278,324 A | 1/1994 | Kingston et al. |
| 5,658,785 A | 8/1997 | Johnson |
| 5,731,288 A | 3/1998 | Markland et al. |
| 5,814,609 A | 9/1998 | Markland et al. |
| 6,034,072 A | 3/2000 | Ralston et al. |
| 6,040,174 A | 3/2000 | Imler et al. |
| 6,040,295 A | 3/2000 | Rolland et al. |
| 6,110,744 A | 8/2000 | Fang et al. |
| 6,133,029 A | 10/2000 | Gruber et al. |
| 6,147,055 A | 11/2000 | Hobart et al. |
| 6,294,374 B1 | 9/2001 | Sinha et al. |
| 6,365,749 B1 | 4/2002 | Kim et al. |
| 6,380,394 B1 | 4/2002 | Nicolaou et al. |
| 6,380,395 B1 | 4/2002 | Vite et al. |
| 6,387,664 B1 | 5/2002 | Ikemoto |
| 6,387,927 B1 | 5/2002 | Altmann et al. |
| 6,399,638 B1 | 6/2002 | Vite et al. |
| 6,440,944 B2 | 8/2002 | Bruder et al. |
| 6,441,186 B1 | 8/2002 | Nicolaou et al. |
| 6,489,314 B1 | 12/2002 | Ashley et al. |
| 6,498,257 B1 | 12/2002 | Vite et al. |
| 6,518,421 B1 | 2/2003 | Li et al. |
| 6,531,497 B1 | 3/2003 | Nicolaou et al. |
| 6,537,988 B2 | 3/2003 | Lee |
| 6,566,128 B1 | 5/2003 | Graham et al. |
| 6,583,290 B1 | 6/2003 | Julien et al. |
| 6,589,968 B2 | 7/2003 | Arslanian et al. |
| 6,596,875 B2 | 7/2003 | White et al. |
| 6,605,599 B1 | 7/2003 | Vite et al. |
| 6,605,726 B1 | 8/2003 | Mulzer et al. |
| 6,610,736 B1 | 8/2003 | Klar et al. |
| 6,624,310 B1 | 9/2003 | Hoefle et al. |
| 6,638,742 B1 | 10/2003 | Hoffman |
| 6,660,758 B1 | 12/2003 | Nicolaou et al. |
| 6,669,942 B2 | 12/2003 | Perricaudet et al. |
| 6,670,384 B2 | 12/2003 | Bandyopadhyay et al. |
| 6,686,380 B2 | 2/2004 | Lee |
| 6,689,802 B2 | 2/2004 | DiMarco et al. |
| 6,710,030 B1 | 3/2004 | Markland et al. |
| 6,710,035 B2 | 3/2004 | Felgner et al. |
| 6,719,540 B2 | 4/2004 | Regueiro-Ren et al. |
| 6,727,276 B2 | 4/2004 | Lee |
| 6,730,803 B2 | 5/2004 | Iwasaki et al. |
| 6,780,620 B1 | 8/2004 | Li et al. |
| 6,794,188 B2 | 9/2004 | Barsov et al. |

(Continued)

FOREIGN PATENT DOCUMENTS

| | | |
|---|---|---|
| DE | 197 13 213 | 10/1998 |
| JP | 2000-245467 | 9/2000 |

(Continued)

OTHER PUBLICATIONS

US Notice of Allowance dated Oct. 4, 2011 in U.S. Appl. No. 12/831,226.
Altmann et al. Microtublule stabilizing agents: a growing class of important anticancer drugs. Curr Opin Chem Biol. 5(4):424-31 (2001).
Niewiarowski et al., Disintegrins and Other Naturally Occurring Antagonists of Platelet Fibrinogen Receptors, Seminars in Hematology, 31(4):289-300 (1994).

(Continued)

*Primary Examiner* — Nancy T Vogel
(74) *Attorney, Agent, or Firm* — Foley & Lardner LLP; Antoinette F. Konski

(57) ABSTRACT

Provided herein are methods for expressing proteins with disulfide bridges such as Vicrostatin (VCN), a chimeric variant of native snake venom disintegrin Contortrostatin (CN). The methods include what is believed to be a more efficient natural selection process that results in generating increased amounts of correctly-folded active conformers of proteins with disulfide bridges. In an aspect, this is achieved by growing Origami B cells in a more optimal redox environment during the induction of heterologous recombinant protein production.

21 Claims, 10 Drawing Sheets

(56) References Cited

U.S. PATENT DOCUMENTS

| | | | |
|---|---|---|---|
| 6,800,653 B2 | 10/2004 | Regueiro-Ren et al. |
| 6,831,090 B2 | 12/2004 | Vite et al. |
| 6,858,411 B1 | 2/2005 | Julien et al. |
| 6,867,333 B2 | 3/2005 | Wessjohann et al. |
| 6,878,699 B1 | 4/2005 | Hemscheidt et al. |
| 6,893,859 B2 | 5/2005 | Ashley et al. |
| 6,900,331 B2 | 5/2005 | Taylor et al. |
| 6,906,188 B2 | 6/2005 | White et al. |
| 6,921,650 B1 | 7/2005 | Julien et al. |
| 6,930,102 B2 | 8/2005 | Klar et al. |
| 6,930,187 B2 | 8/2005 | Favreau et al. |
| 6,958,401 B2 | 10/2005 | White et al. |
| 6,982,276 B2 | 1/2006 | DiMarco et al. |
| 6,982,280 B1 | 1/2006 | Hoefle et al. |
| 6,998,256 B2 | 2/2006 | Arslanian |
| 7,008,936 B2 | 3/2006 | Voi et al. |
| 7,220,724 B2 | 5/2007 | Markland et al. |
| 2002/0042109 A1 | 4/2002 | Vite et al. |
| 2002/0045609 A1 | 4/2002 | Ashley et al. |
| 2002/0062030 A1 | 5/2002 | White et al. |
| 2002/0094991 A1 | 7/2002 | Gallaher |
| 2002/0143038 A1 | 10/2002 | Bandyopadhyay et al. |
| 2002/0156110 A1 | 10/2002 | Arslanian et al. |
| 2002/0165257 A1 | 11/2002 | Lee |
| 2002/0165258 A1 | 11/2002 | Lee |
| 2002/0169190 A1 | 11/2002 | Bandyopadhyay et al. |
| 2002/0188014 A1 | 12/2002 | DiMarco et al. |
| 2002/0193361 A1 | 12/2002 | Ashley et al. |
| 2003/0004338 A1 | 1/2003 | Li et al. |
| 2003/0023082 A1 | 1/2003 | Ashley et al. |
| 2003/0045711 A1 | 3/2003 | Ashley et al. |
| 2003/0060623 A1 | 3/2003 | Vite et al. |
| 2003/0073677 A1 | 4/2003 | Lee |
| 2003/0087888 A1 | 5/2003 | Regueiro-Ren et al. |
| 2003/0144523 A1 | 7/2003 | Klar et al. |
| 2003/0144533 A1 | 7/2003 | Iwasaki et al. |
| 2003/0149281 A1 | 8/2003 | Westermann et al. |
| 2003/0176473 A1 | 9/2003 | Taylor et al. |
| 2003/0176710 A1 | 9/2003 | Klar et al. |
| 2003/0186334 A1 | 10/2003 | Marcinkiewicz |
| 2003/0186884 A1 | 10/2003 | Markland et al. |
| 2003/0186965 A1 | 10/2003 | Vite et al. |
| 2003/0187039 A1 | 10/2003 | Favreau et al. |
| 2003/0187273 A1 | 10/2003 | White et al. |
| 2003/0191089 A1 | 10/2003 | Regueiro-Ren et al. |
| 2003/0203938 A1 | 10/2003 | Nicolaou et al. |
| 2003/0219877 A1 | 11/2003 | Tang et al. |
| 2003/0220295 A1 | 11/2003 | Vite et al. |
| 2003/0220503 A1 | 11/2003 | Mulzer et al. |
| 2004/0014978 A1 | 1/2004 | Klar et al. |
| 2004/0022869 A1 | 2/2004 | Chen et al. |
| 2004/0023345 A1 | 2/2004 | Vite et al. |
| 2004/0024032 A1 | 2/2004 | Voi et al. |
| 2004/0029781 A1 | 2/2004 | Hernan et al. |
| 2004/0030147 A1 | 2/2004 | White et al. |
| 2004/0038324 A1 | 2/2004 | Atadja et al. |
| 2004/0039026 A1 | 2/2004 | Nicoloou et al. |
| 2004/0043387 A1 | 3/2004 | Liu et al. |
| 2004/0049051 A1 | 3/2004 | Hoefle et al. |
| 2004/0052785 A1 | 3/2004 | Goodman et al. |
| 2004/0053978 A1 | 3/2004 | Lee et al. |
| 2004/0058969 A1 | 3/2004 | Buchmann et al. |
| 2004/0072870 A1 | 4/2004 | Nicolaou et al. |
| 2004/0072882 A1 | 4/2004 | Johnson et al. |
| 2004/0082651 A1 | 4/2004 | Wessjohann et al. |
| 2004/0092478 A1 | 5/2004 | Rothermel et al. |
| 2004/0127432 A1 | 7/2004 | Nicolaou et al. |
| 2004/0132146 A1 | 7/2004 | Benigni et al. |
| 2004/0132754 A1 | 7/2004 | Brandt et al. |
| 2004/0157897 A1 | 8/2004 | DiMarco et al. |
| 2004/0176429 A1 | 9/2004 | Li et al. |
| 2004/0214871 A1 | 10/2004 | Lee |
| 2004/0253697 A1 | 12/2004 | Julien et al. |
| 2004/0259922 A1 | 12/2004 | Hoefle et al. |
| 2005/0038086 A1 | 2/2005 | Ashley et al. |
| 2005/0042275 A1 | 2/2005 | Sonntag et al. |
| 2005/0113429 A1 | 5/2005 | Klar et al. |
| 2005/0148657 A1 | 7/2005 | Zygmunt et al. |
| 2005/0159461 A1 | 7/2005 | Lee |
| 2005/0187270 A1 | 8/2005 | Klar et al. |
| 2005/0192440 A1 | 9/2005 | White et al. |
| 2005/0214259 A1 | 9/2005 | Sano et al. |
| 2005/0267306 A1 | 12/2005 | Westermann et al. |
| 2005/0282873 A1 | 12/2005 | Rothermel |
| 2006/0013836 A1 | 1/2006 | Bandyopadhyay et al. |
| 2006/0014796 A1 | 1/2006 | Denni-Dischert et al. |
| 2006/0040990 A1 | 2/2006 | Klar et al. |
| 2006/0046997 A1 | 3/2006 | Klar et al. |
| 2006/0063815 A1 | 3/2006 | DiMarco et al. |
| 2006/0246541 A1 | 11/2006 | Minea et al. |
| 2007/0093878 A1 | 4/2007 | Edge et al. |
| 2007/0123458 A1 | 5/2007 | Markland et al. |
| 2007/0254361 A1 | 11/2007 | Tsai |
| 2008/0064634 A1 | 3/2008 | Markland et al. |
| 2008/0305320 A1 | 12/2008 | Laude et al. |
| 2008/0306611 A1 | 12/2008 | Rowley et al. |
| 2008/0317763 A1 | 12/2008 | Lackmann et al. |
| 2011/0300579 A1 | 12/2011 | Minea et al. |
| 2012/0142603 A1 | 6/2012 | Markland et al. |
| 2013/0045244 A1 | 2/2013 | Minea et al. |

FOREIGN PATENT DOCUMENTS

| | | |
|---|---|---|
| JP | 2004-500357 | 1/2004 |
| JP | 2004-217535 | 8/2004 |
| WO | WO-00/18421 | 4/2000 |
| WO | WO-01/41791 | 6/2001 |
| WO | WO 2004/095027 A1 | 11/2004 |
| WO | WO 2010/093468 | 8/2010 |
| WO | WO-2011/100362 | 8/2011 |

OTHER PUBLICATIONS

Office Action in U.S. Appl. No. 13/219,472 dated Nov. 21, 2012.
Aslund et al., The Thioredoxin Superfamily: Redundancy, Specificity and Gray-Area Genomics, Journal of Bacteriology 181(5):1375-1379 (1999).
Bader et al., Disulfide Bonds are Generated by Quinone Reduction, The Journal of Biological Chemistry 275(34):26082-26088 (2000).
Bader et al., Oxidative Protein Folding is Driven by the Electron Transport System, Cell 98:217-227 (1999).
Bader et al., Reconstitution of a Protein Disulfide Catalytic System, The Journal of Biological Chemistry 273(17):10302-10307 (1998).
Bader et al., Turning a Disulfide Isomerase into an Oxidase: DsbC Mutants that Imitate DsbA, The EMBO Journal 20(7):1555-1562 (2001).
Baneyx, Recombinant Protein Expression in *Escherichia coli*, Current Opinion in Biotechnology 10:411-421 (1999).
Bardwell et al., A Pathway for Disulfide Bond Formation In Vivo, Proc. Natl. Acad. Sci. USA 90:1038-1042 (1993).
Bardwell et al., Identification of a Protein Required for Disulfide Bond Formation In Vivo, Cell 67:581-589 (1991).
Becker et al., Expression, Secretion and Folding of Human Growth Hormone in *Escherichia coli*, FEBS 204(1):145-150 (1986).
Bessette et al., Effect of Sequences of the Active-Site Dipeptides of DsbA and DsbC on In Vivo Folding of Multidisulfide Proteins in *Escherichia coli*, Journal of Bacteriology 183(3):980-988 (2001).
Bessette et al., Efficient Folding of Proteins with Multiple Disulfide Bonds in the *Escherichia coli* Cytoplasm, PNAS 96:13703-13708 (1999).
Bessette et al., In Vivo and In Vitro Function of the *Escherichia coli* Periplasmic Cysteine Oxidoreductase DsbG, The Journal of Biological Chemistry 274(12):7784-7792 (1999).
Bilgrami et al., Crystal Structure of Schistatin, a Disintegrin Homodimer from Saw-Scaled Viper (*Echis carinatus*) at 2.5 ? Resolution, J. Mol. Biol. 341:829-837 (2004).
Branden et al., Introduction to Protein Structure Second Edition, Garland Publishing Inc., New York, 1999, pp. 374,375,382.
Bridges et al., Integrin a4β1-Dependent adhesion to ADAM 28 (MDC-L) requires an extended surface of the disintegrin domain. Biochemistry 42:3734-3741, 2003.

(56) References Cited

OTHER PUBLICATIONS

Calvete et al., Disulphide-Bond Pattern and Molecular Modelling of the Dimeric Disintegrin EMF-10, a Potent and Selective Integrin x5β1 Antagonist from *Eristocophis macmahoni* Venom, Biochem. J. 345:573-581 (2000).
Chao et al., *Agkistrodon piscivorus* piscivorus platelet aggregation inhibitor: A potent inhibitor of platelet activation, Proc. Natl. Acad. Sci. USA, 86:8050-8054 (1989).
Chen et al., Chaperone Activity of DsbC, The Journal of Biological Chemistry 274(28):19601-19605 (1999).
Chivers et al., General Acid/Base Catalysis in the Active Site of *Escherichia coli* Thioredoxin, Biochemistry 36:15810-15816 (1997).
Chivers et al., The CXXC Motif: A Rheostat in the Active Site, Biochemistry, 36(14):4061-4066 (1997).
Choudhary et al., Two New Rearranged Taxoids from *Taxus wallichiana* Zucc, Chem. Pharm. Bull., 50(11): 1488-1490 (2002).
Chung et al., Transfer of Electrons Across the Cytoplasmic Membrane by DsbD, a Membrane Protein Involved in Thiol-Disulphide Exchange and Protein Folding in the Bacterial Periplasm, Molecular Microbiology, 35(5):1099-1109 (2000).
Collet et al, Disulfides Out of Thin Air, Nature Structural Biology, 9:2-3 (2002).
Collet et al, Oxidative Protein Folding in Bacteria, Molecular Microbiology, 44(1)1-8 (2002).
Collet et al., Reconstitution of a Disulfide Isomerization System, The Journal of Biological Chemistry, 277(30):26886-26892 (2002).
Connolly et al., The snake venom protein s-echistatin inhibits platelet adhesion to collagen by both an RGD-dependent and -independent mechanisms, vol. 82, No. 4, (Suppl. III), pp. 660 (1990).
Darby et al., Identifying and Characterizing a Second Structural Domain of Protein Disulfide Isomerase, FEBS Letters 448:167-172 (1999).
Di Luccio et al., Parameters Affecting in Vitro Oxidation/Folding of Maurotoxin, a Four-Disulphide-Bridged Scorpion Toxin, Biochem. J., 358:681-692 (2001).
Dubendorff et al., Controlling Basal Expression in an Inducible T7 Expression System by Blocking the Target T7 Promoter with Lac Repressor, J. Mol. Biol., 219:45-59 (1991).
European Search Report dated Dec. 30, 2009 for EP Application No. 06849695.9.
Ferrero et al., The Platelet Endothelial Cell Adhesion Molecule-1 (PECAM1) Contributes to Endothelial Barrier Function, FEBS Letters, 374:323-326 (1995).
Frydman, Folding of Newly Translated Proteins In Vivo: The Role of Molecular Chaperones, Annu. Rev. Biochem., 70:603-647 (2001).
Fujii et al., Crystal Structure of Trimestatin, a Disintegrin Containing a Cell Adhesion Recognition Motif RGD, J. Mol. Biol., 332:1115-1122 (2003).
Fujii et al., The Formation of Amphotericin B Ion Channels in Lipid Bilayers, Biochemistry, 36:4959-4968 (1997).
Gan et al., A Potent Platelet Aggregation Inhibitor From the Venom of the Viper, *Echis Carinatus*, J. Biol. Chem. 263(36):19827-19832 (1988).
Georgiou et al., Expression of Correctly Folded Proteins in *Escherichia coli*, Current Opinion in Biotechnology, 7:190-197 (1996).
Giannakakou et al., A common pharmacophore for epothilone and taxanes: Molecular basis for drug resistance conferred by tubulin mutations in human cancer cells, PNAS 97(6):2904-2909 (2000).
Goldstone et al., DsbC Activation by the N-Terminal Domain of DsbD, PNAS 98,(17):9551-9556 (2001).
Golubkov et al., Anti-angiogenic activity of contortrostatin, a disintegrin from *Agkistrodon contortrix* contortrix snake venom, Angiogenesis 6:213-224 (2003).
Gordon et al., *Escherichia coli* DipZ: Anatomy of a Transmembrane Protein Disulphide Reductase in Which Three Pairs of Cysteine Residues, One in Each of Three Domains, Contribute Differentially to Function, Molecular Microbiology, 35(6):1360-1374 (2000).

Goulding et al., Thiol-Disulfide Exchange in an Immunoglobulin-Like Fold: Structure of the N-Terminal Domain of DsbD, Biochemistry, 41:6920-6927 (2002).
Grauschopf, et al., Why is DsbA Such an Oxidizing Disulfide Catalyst?, Cell, 83:947-955 (1995).
Gross et al., A New FAD-Binding Fold and Intersubunit Disulfide Shuttle in the Thiol Oxidase Erv2p, Nature Structural Biology, 9(1):61-67 (2002).
Guddat et al., Crystal Structures of Reduced and Oxidized DsbA: Investigation of Domain Motion and Thiolate stabilization, Structure, 6:757-767 (1998).
Guddat et al., The Uncharged Surface Features Surrounding the Active Site of *Escherichia coli* DsbA are Conserved and are Implicated in Peptide Binding, Protein Science, 6:1148-1156 (1997).
Guerdoux-Jamet et al., Using Codon Usage to Predict Genes Origin: Is the *Escherichia coli* Outer Membrane a Patchwork of Products form Different Genomes?, DNA Research, 4:257-265 (1997).
Haebel et al., The Disulfide Bond Isomerase DsbC is Activated by an Immunoglobulin-Fold Thiol Oxidoreductase: Crystal Structure of the DsbC-DsbD? Complex, The Embo Journal, 21(18):4774-4784 (2002).
Holahan et al., Prevention of Reocculsion following Tissue Type Plasminogen Activator-Induced Thrombolysis by the TDD-Containing Peptide, Echistatin, in a Canine Model of Coronary Thrombosis, Pharmacology 42:340-348 (1991).
Holmgren, Thiroedoxin Structure and Mechanism: Conformational Changes on Oxidation of the Active-Site Sulfhydryls to a Disulfide, Structure, 3:239-243 (1995).
Holton et al., First Total Synthesis of Taxol. 1 Functionalization of the B Ring, J. Am. Chem. Soc. 116:1597-1598 (1994).
Hoshino et al., Production of Brain-Derived Neurotrophic Factor in *Escherichia coli* by Coexpression of Dsb Proteins, Biosci. Biotechnol. Biochem., 66(2):344-350 (2002).
Huang et al., A Low Molecular Weight Peptide Inhibiting Fibrinogen Interaction With Platelet Receptors Expressed on Glycoprotein IIb-IIIa Complex, J. Biol. Chem. 262(33):16157-16163 (1987).
International Search Report dated Jun. 2, 2008 for PCT Application No. PCT/US06/04413.
Interview Summary dated Aug. 11, 2009 for U.S. Appl. No. 11/351,311.
Jennewein et al., Taxol biosynthesis: Taxine 13;1-hydroxylase is a cytochrome P450-dependent monooxygenase, PNAS 98(24):13595-13600 (2001).
Jurado et al., Production of Functional Single-Chain Fv Antibodies in the Cytoplasm of *Escherichia coli*, J. Mol. Biol., 320:1-10 (2002).
Kadokura, et al., Protein Disulfide Bond Formation in Prokaryotes, Annu. Rev. Biochem., 72:111-135 (2003).
Kang et al., A Novel Disintegrin Sal mosin Inhibits Tumor Angiogenesis, Cancer Research 59:3754-60 (1999).
Kassab et al, Cloning, expression, and structural analysis of recombinant BJcuL, a c-type lectin from the *Bothrops jararacussu* snake venom, Protein Expression and Purification, vol. 35, No. 2, pp. 344-352, 2004.
Katzen et al., Role and Location of the Unusual Redox-Active Cysteines in the Hydrophobic Domain of the Transmembrane Electron Transporter DsbD, PNAS, 100(18):10471-10476 (2003).
Katzen et al., Transmembrane Electron Transfer by the Membrane Protein DsbD Occurs Via a Disulfide Bond Cascade, Cell, 103:769-779 (2000).
Kemmink et al., The Folding Catalyst Protein Disulfide Isomerase is Constructed of Active and Inactive Thioredoxin Molecules, Current Biology, 7:239-245 (1997).
Kim et al., Efficient Production of a Bioactive, Multiple Disulfide-Bonded Protein Using Modified Extracts of *Escherichia coli*, Biotechnology and Bioengineering, 85:122-129 (2004).
Kisselev, Polypeptide release factors in prokaryotes and eukaryotes: same function, different structure, Structure, 10:8-9, 2002.
Kowalski et al., The Microtubule-Stabilizing Agent Discodermolide Competitively Inhibits the Binding of Paclitaxel (Taxol) to Tubulin Polymers, Enhances Tubulin Nucleation Reactions More Potently than Paclitaxel, and Inhibits the Growth of Paclitaxel-Resistant Cells, Mol. Pharm. 52:613-622 (1997).

(56) References Cited

OTHER PUBLICATIONS

Kurokawa et al., Overexpression of Protein Disulfide Isomerase DsbC Stabilizes Multiple-Disulfide-Bonded Recombinant Protein Produced and Transported to the Periplasm in *Escherichia coli*, Applied and Environmental Microbiology, 66(9):3960-3965 (2000).
Kurokawa et al., Overproduction of Bacterial Protein Disulfide Isomerase (DsbC) and Its Modulator (DsbD) Markedly Enhances Periplasmic Production of Human Nerve Growth Factor in *Escherichia coli*, Journal of Biological Chemistry, 276(17):14393-14399 (2001).
LaVallie et al., A Thioredoxin Gene Fusion Expression System That Circumvents Inclusion Body Formation in the *E. coli* Cytoplasm, Bio/Technology, 11:187-193 (1993).
Levy et al., Gemcitabine plus docetaxel: a new treatment option for anthracycline pretreated metastatic breast cancer patients?, Cancer Treat. Rev., vol. 31 (Suppl. 4), pp. S17-S22 (2005).
Levy et al., Production of Correctly Folded Fab Antibody Fragment in the Cytoplasm of *Escherichia coli* trxB gor Mutants via the Coexpression of Molecular Chaperones, Protein Expression and Purification, 23:338-347 (2001).
Liu et al., Disulfide-Dependent Folding and Export of *Escherichia coli* DsbC, The Journal of Biological Chemistry, 276(2):1146-1151 (2001).
Madiraju et al., Tubulin Assembly, Taxoid Site Binding, and Cellular Effects of the Microtubule-Stabilizing Agent Dictyostatin, Biochem. 44:15053-15063 (2005).
Makrides, Strategies for Achieving High-Level Expression of Genes in *Escherichia coli*, Microbiological Reviews, American Society for Microbiology, Washington, DC, US, 60(3):512-538, 1996.
Mani et al., Phase I Clinical and Pharmacokinetic Study of BMS-247550, a Novel Derivative of Epothilone B, in Solid, Tumors, Clin. Cancer Res. 10:1289-1298 (2004).
Markland et al, Snake Venom Disintegrin: An Effective Inhibitor of Breast Cancer Growth and Dissemination, Chapter 18 in Natural and Selected Synthetic Toxins, Biological Implications, Tu, A.T. et al. editors, ACS Symposium Series, 745:262-282 (2000).
Markland et al., A Novel Snake Venom Disintegrin That Inhibits Human Ovarian Cancer Dissemination and Angiogenesis in an Orthotopic Nude Mouse Model, Haemostasis 31(3-6): 183-191 (2001).
Martin et al., Crystal Structure of the DsbA Protein Required for Disulphide Bond Formation in Vivo, Nature, 365:464-468 (1993).
Martin, Thioredoxin—A Fold for All Reasons, Structure, 3:245-250 (1995).
Maskos et al., DsbA and DsbC—Catalyzed Oxidative Folding of Proteins with Complex Disulfide Bridge Patterns In Vitro and In Vivo, J. Mol. Biol., 325:495-513 (2003).
Mattern et al., Giloma cell integrin expression and their interactions with integrin antagonists, Cancer Therapy, 3:325-340, 2005.
McCarthy et al., Crystal Structure of the Protein Disulfide Bond Isomerase, DsbC, from *Escherichia coli*, Nature America Inc., 7(3):196-199 (2000).
McLane et al., Proceedings of the Society for Experimental Biology and Medicine, Proc. Soc. Exp. Biol. Med., 219(2):109-119 (1998).
McLane et al., Viper Venom Disintegrins and Related Molecules, Proc Soc. Exp. Biol. Med. 219(2):109-119 (1998).
Missiakas et al., Protein Folding in the Bacterial Periplasm, Journal of Bacteriology, 179(8):2465-2471 (1997).
Missiakas et al., Protein Misfolding in the Cell Envelope of *Escherichia coli*: New Signaling Pathways, TIBS, 22:59-63 (1997).
Missiakas et al., The *Escherichia coli* dsbC (xprA) Gene Encodes a Periplasmic Protein Involved in Disulfide Bond Formation, The EMBO Journal, 13(8):2013-2020 (1994).
Moiseeva et al., Purification, Crystallization and Preliminary X-Ray Analysis of the Disintegrin Contortrostatin From *Agkistrodon contortrix* Contortrix Snake Venom, Acta Cryst., D58:2122-2124 (2002).
Mooberry et al., Microtubule-stabilizing agents based on designed laulimalide analogues, PNAS 101(23) 8803-8808 (2004).

Mössner et al., Characterization of *Escherichia coli* Thioredoxin Variants Mimicking the Active-Sites of Other Thiol/Disulfide Oxidoreductases, Protein Science, 7:1233-1244 (1998).
Mössner et al., Importance of Redox Potential for the In Vivo Function of the Cytoplasmic Disulfide Reductant Thioredoxin from *Escherichia coli*, The Journal of Biological Chemistry 274(36):25254-25259 (1999).
Mössner et al., Influence of the pKa Value of the Buried, Active-Site Cysteine on the Redox Properties of Thioredoxin-Like Oxidoreductases, FEBS Letters, 477:21-26 (2000).
Moura-da-Silva et al., Jararhagin ECD-Containing Disintegrin Domain: Expression in *Escherichia coli* and and Inhibition of the Platelet-Collagen Interaction Archives of Biochemistry and Biophysics, vol. 369, No. 2, Sep. 15, 1999, pp. 295-301.
NCBI protein search result of "disintegrin", Retrieved from the Internet <URL:http://www.ncbi.nlm.nih.gov/ sites/entrez>, 2009.
O'Brien et al., The Adaptability of *Escherichia coli* Thioredoxin to Non-Convervative Amino Acid Substitutions, Protein Sci., 6:1325-1332 (1997).
Ono et al., Absorption, Distribution, and Excretion of DJ-927, A Novel Orally Effective Taxane, in Mice, Dogs, and Monkeys, Biol. Pharm. Bull. 27(3): 345-351 (2004).
Pinski et al., A novel therapy for prostate cancer based on the disintegrin contortrostatin, Proc. Am. Soc. Clin. Oncol. 22, (Abstract—1 pg.) (2003).
Prinz et al., The Role of the Thioredoxin and Glutaredoxin Pathways in Reducing Protein Disulfide Bonds in the *Escherichia coli* Cytoplasm, The Journal of Biological Chemistry, 272(25):15661-15667 (1997).
Raina et al., Making and Breaking Disulfide Bonds, Annu. Rev. Microbiol., 51:179-202 (1997).
Rietsch et al., An In Vivo Pathway for Disulfide Bond Isomerization in *Escherichia coli*, Proc. Natl. Acad. Sci. USA, 93:13048-13053 (1996).
Rietsch et al., Reduction of the Periplasmic Disulfide Bond Isomerase, DsbC, Occurs by Passage of Electrons from Cytoplasmic Thioredoxin, Journal of Bacteriology, 179(21):6602-6608 (1997).
Ritz et al., Roles of Thiol-Redox Pathways in Bacteria, Annu. Rev. Microbiol., 55:21-48 (2001).
Ritz et al., Thioredoxin 2 is Involved in the Oxidative Stress Response in *Escherichia coli*, The Journal of Biological Chemistry, 275(4):2505-2512 (2000).
Rorrer et al, Autocatalytic Activity of the Tobacco Etch Virus Nla Proteinase in Viral and Foreign Protein Sequences, Journal of General Virology, vol. 73, No. 4, pp. 775-783, 1992.
Rose et al., Therapeutic Synergy of Oral Taxane BMS-275183 and Cetuximab versus Human Tumor Xenografts, Clin. Cancer Res. 10:7413-7417 (2004).
Sampath et al., MAC-321, a novel taxane with greater efficacy than paclitaxel and docetaxel in vitro and in vivo, Mol. Cancer Ther. 2(9):873-74 (2003).
Savage et al., Binding of the Snake Venom-derived Proteins Applaggin and Echistatin to the Arginine-Glycine-Aspartic Acid Recognition Site(s) on Platelet Glycoprotein IIb-IIIa Complex Inhibits Receptor Function, J. Biol. Chem. 265(20):11766-11772 (1990).
Scarborough et al., A GPIIb-IIIa-Specific Integrin Antagonist From the Venom of Sistrurus M. Barbouri, J. Biol. Chem. 266(15):9359-9362 (1991).
Schäfer et al., Skp, a Molecular Chaperone of Gram-Negative Bacteria, is Required for the Formation of Soluble Periplasmic Intermediates of Outer Membrane Proteins, The Journal of Biological Chemistry, 274(35):24567-24574.
Schmitmeier et al., Anti-invasive Effect of Contortrostatin, a Snake Venom Disintegrin, and TNF-;1 on Malignant Glioma Cells, Anticancer Res. 20:4227-4233 (2000).
Shebuski et al., Acceleration of Recombinant Tissue-Type Plasminogen Activator-Induced Thrombolysis and Prevention of Reocclusion by the Combination of Heparin and the Arg-Gly-Asp-Containing Peptide Bitistatin in a Canine Model of Coronary Thrombosis, Circulation 82(1):169-177 (1990).
Shen et al., New Bicyclic Taxane Diterpenoids from *Taxus sumatrana*, Chem. Pharm. Bull. 53(7):808-810 (2005).

(56) References Cited

OTHER PUBLICATIONS

Stewart et al., Disulfide Bond Formation in the *Escherichia coli* Cytoplasm: an In Vivo Role Reversal for the Thioredoxins, The EMBO Journal, 17(19):5543-5550 (1998).
Studier et al., Use of T7 RNA Polymerase to Direct Expression of Cloned Genes, Methods in Enzymology, 185:60-89 (1990).
Studier, Use of Bacteriophage T7 Lysozyme to Improve an Inducible T7 Expression System, J. Mol. Biol., 219:37-44 (1991).
Swartz, Advances in *Escherichia coli* Production of Therapeutic Proteins, Current Opinion in Biotechnology, 12:195-201 (2001).
Swenson et al., Chimeric derivative of fibrolase, a fibrinolytic enzyme from southern copperhead venom, possesses inhibitory activity on platelet aggregation, Arch. Biochem. Biophys., (2000), 384(2):227-237.
Swenson et al., Intravenous Liposomal Delivery of the Snake Venom Disintegrin Contortrostatin Limits Breast Cancer Progression, Mol. Cancer Ther., 3(4):499-511 (2004).
Trikha et al, Inhibition of tumor cell binding to fibronectin in the presence of snake venom disintegrins, Proc Annu. Meet. Am Assoc Cancer Res. Meeting Abstract, vol. 33, pp. 34—Cancerlit Database, Abstract No. 92682733, 1992.
Trikha et al., A Novel Platelet aggregation inhibitor from southern copperhead snake venom, Fibrinolysis, vol. 4 (Suppl. 1):105 (1990).
Trikha et al., Characterization of a Novel Platelet Aggregation Inhibitor (Contortrostatln) From the Southern Copperhead Snake Venom, Blood, vol. 76, No. 10 (Suppl. 1):479a (1990).
Trikha et al., Contortrostatin, a Snake Venom Disintegrin, Inhibits Beta1 Integrin-mediated Human Metastatic Melanoma Cell Adhesion and Blocks Experimental Metastasis, Cancer Res. 54: 4993-4998 (1994).
Trikha et al., Purification and Characterization of Platelet Aggregation Inhibitors From Snake Venoms, Thrombosis Res., 73(1):39-52 (1994).
US Notice of Allowance dated Feb. 4, 2010 for U.S. Appl. No. 11/351,311.
US Notice of Allowance dated Aug. 24, 2009 for U.S. Appl. No. 11/351,311.
US Office Action dated Feb. 19, 2008 for U.S. Appl. No. 11/351,311.
US Office Action dated May 8, 2009 for U.S. Appl. No. 11/351,311.
US Office Action dated Sep. 4, 2008 for U.S. Appl. No. 11/351,311.
Vella et al., A Recombinant Chimeric Epidermal Growth Factor-like Module with High Binding Affinity for Integrins, J Biol Chem., May 30, 2003; 278(22):19834-19843.
Venturi et al., High Level Production of Functional Antibody Fab Fragments in an Oxidizing Bacterial Cytoplasm, J. Mol. Biol., 315:1-8 (2002).
Villalva-Servin et al., Part 2: Efficient strategies for the construction of variably substituted bicyclo[5.3.1]undecenones (AB-taxane right systems) and their conversion to tricyclo[9.3.1. 03,8]pentadecoenones (ABC taxane right systems) and bicyclo[2.2.2]octanones, Can. J. Chem. 82:227-239 (2004).
Walker et al., Effect of Redox Environment on the In Vitro and In Vivo Folding of RTEM-1 β-Lactamase and *Escherichia coli* Alkaline Phosphatase, The Journal of Biological Chemistry, 269(45):28487-28493 (1994).
Wang et al., A Unique Approach for High Level Expression and Production of a Recombinant Cobra Neurotoxin in *Escherichia coli*, Journal of Biotechnology, 94:235-244 (2002).
Wierzbicka-Patynowski et al., Structural Requirements of Echistatin for the Recognition of alphavβ3 and alpha5β1 Integrins, The Journal of Biological Chemistry, 274(53):37809-37814 (1999).
Wishart et al., A single mutation converts a novel phosphotyrosine binding domain into a dual-specificity phosphatase, Journal of Biological Chemistry, 270(45):26782-26785, 1995.
Witkowski et al., Conversion of a beta-ketoacyl synthase to a malonyl decarboxylase by replacement of the active-site cysteine with glutamine, Biochemistry, 38:11643-11650, 1999.
Wolff et al., Phase I Study of Docosahexaenoic Acide-Paclitaxel: A Taxane-Fatty Acid Conjugate with a Unique Pharmacology and Toxicity Profile, Clin. Cancer Res. 9:3589-3597 (2003).
Woycechowsky et al., The CXC Motif: A Functional Mimic of Protein Disulfide Isomerase, Biochemistry, 42:5387-5394 (2003).
Yasuda et al, Comparative Effects of Aspirin, a Synthetic Thrombin Inhibitor and a Monoclonal Antiplatelet Glycoprotein IIb/IIIa Antibody on Coronary Artery Reperfusion, Reocclusion and Bleeding With Recombinant Tissue-Type Plasminogen Activator in a Canine Preparation, JACC 16(3):714-722 (1990).
Yasuda et al., Kistrin, A Polypeptide Platelet GPIIb/IIIa Receptor Antagonist, Enhances and Sustains Coronary Arterial Thrombolysis With Recombinant Tissue-Type Plasminogen Activator in a Canine Preparation, Circulation 83(3):1038-1047 (1991).
Yasukawa et al, Increase of solubility of foreign proteins in *Escherichia coli* by coproduction of the bacterial thioredoxin, Journal of Biological Chemistry, vol. 270, No. 43, pp. 25328-25331, 1995.
Yeh et al, Accutin, a New Disintegrin, Inhibits Angiogenesis In Vitro and In Vivo by Acting as Integin alphavalpha3 Antagonist and Inducing Apoptosis, Blood, vol. 92, No. 9, pp. 3268-3276 (1998).
Yuan et al, The role of thioredoxin and disulfide isomerase in the expression of the snake venom thrombin-like enzyme calobin in *Escherichia coli* BL21 (DE3), Protein Expression and Purification, vol. 38, No. 1, pp. 51-60, 2004.
Zapun et al., Structural and Functional Characterization of DsbC, a Protein Involved in Disulfide Bond Formation in *Escherichia coli*, Biochemistry, 34:5075-5089 (1995).
Zapun et al., The Reactive and Destabilizing Disulfide Bond of DsbA, a Protein Required for Protein Disulfide Bond Formation in Vivo, Biochemistry, 32:5083-5092 (1993).
Zhang et al., Expression of Eukaryotic Proteins in Soluble Form in *Escherichia coli*, Prot. Exp. and Purif., 12:159-165 (1998).
Zhang et al., Low-Usage Codons in *Escherichia coli*, Yeast, Fruit Fly and Primates, Gene, 105:61-72 (1991).
Zhao et al., Dimerization by Domain Hybridization Bestows Chaperone and Isomerase Activities, The Journal of Biological Chemistry, 278(44):43292-43298 (2003).
Zhou et al, Contortrostatin, A Snake Venom Protein, Which Is an Inhibitor of Breast Cancer Progression, Molecular Biology of the Cell, No. 7, Suppl., p. 425A (1996).
Zhou et al., Contortrostatin, a dimeric disintegrin from *Agkistrodon contortrix* contortrix, inhibits angiogenesis, Angiogenesis 3(3):259-269 (1999).
Zhou et al., Contortrostatin, a dimeric disintegrin from *Agkistrodon contortrix* contortrix, inhibits breast cancer progression, Breast Cancer Res. Treat. 61:249-260 (2000).
Zhou et al., Contortrostatin, a Homodimeric Disintegrin, Binds to Integrin alphavbeta5, Biochem. Biophys. Res. Commun. 267:350-355 (2000).
Zhou et al., Molecular Cloning and Functional Expression of Contortrostatin, A Homodimeric Disintegrin From Southern Copperhead Snake Venom, Biochem. 375(2): 278-288 (2000).
Ahmed et al, "The extracellular matrix protein TGFB1 induces microtubule stabilization and sensitizes ovarian cancers to paclitaxel," Cancer Cell, 12:514-527 (2007).
Beekman et al, Phase II evaluations of Cilengitide in asymptomatic patients with androgen-independent prostate cancer: scientific rationale and study design, Clinical Genitourinary Cancer, 4(4):299-302 (2006).
Bergstralh et al, "Microtubule stabilizing agents: Their molecular signaling consequences and the potential for enhancement by drug combination," Cancer Treatment Reviews, 32(3):166-179 (2006).
Burgess et al, "Possible dissociation of the heparin binding and mitogenic activities of heparin binding (acidic fibroblast) growth factor 1 from its receptor binding activities by site directed mutagenesis of a single lysine residue," Journal of Cell Biology, 111:2129-2138 (1990).
Burzynski, "Treatment for astrocytic tumors in children: current and emerging strategies," Paediatr. Drugs 8(3):167-178 (2006).
Dyce et al., "Integrins in Head and Neck Squamous Cell Carcinoma Invasion," The Laryngoscope 112:2025-2032 (2002).
Hollebecque et al., "Vascular disrupting agents: a delicate balance between efficacy and side effects," Current Opinion in Oncology 24(3):305-315 (2012).

(56) References Cited

OTHER PUBLICATIONS

Inoue et al, "Docetaxel enhances the therapeutic effect of the angiogenesis inhibitor TNP-470 (AGM-1470) in metastatic human transitional cell carcinoma," Clinical Cancer Research: An Official Journal of the American Associate for Cancer Research, 90:886-899 (2003).

International Preliminary Report on Patentability dated Apr. 15, 2011 for PCT Application No. PCT/US2009/064256.

International Search Report and the Written Opinion dated May 21, 2010 for PCT Application No. PCT/US09/64256.

Juarez et al., "Evolution of Snake Venom Disintegrins by Positive Darwinian Selection," Mol. Bio. Evol. 25(11):2391-2407 (2008).

Kim et al, "Combined anti-angiogenic therapy against VEGF and integrin alpha v beta 3 in an orthotopic model of ovarian cancer," Cancer Biology and Therapy, 8:2261-2270 (2009).

Klaus, "Epitope mapping of ADAMTS13 autoantibodies in acquired thrombotic thrombocytopenic purpura," Blood 103(12):4514-4519 (2004).

Lazar et al., "Transforming growth factor alpha: mutation of aspartic acid 47 and leucine 48 results in different biological activities," Molecular and Cellular Biology, 8(3):1247-1252 (1988).

Li et al., "Correlation of integrin beta 3 mRNA and vascular endothelial growth factor protein expression profiles with the clinicopathological features and prognosis of gastric carcinoma," World J Gastroenterology 14(3):421-427 (2008).

Lu et al., "Integrins in drug targeting-RGD templates in toxins", Current Pharmaceutical Design, 12(22):2749-2769 (2006).

Lutolf et al., "Synthetic biomaterials as instructive extracellular microenvironments for morphogensis in tissue engineering," Nature Biotechnology 23(1):47-55 (2005).

Marcinkiewicz et al., "Significance of RGD Loop and C-terminal Domain of Echistatin for Recognition of 3B1IIb3B2 and 3B1v3B23 Integrins and Expression of Ligand-Induced Binding Site," (1997) Blood, vol. 90, No. 4, pp. 1565-1575.

Marcinkiewicz, Functional characteristic of snake venom disintegrins: potential therapeutic implication, Current Pharmaceutical Design, 11(7):815-827 (2005).

McLane et al., "Disintegrins", Current Drug Targets—Cardiovascular & Haematological Disorders, 4(4):327-355 (2004).

Miles et al, "Combination versus sequential single-agent therapy in metastatic breast cancer," The Oncologist, 7(sup. 6):13-19 (2002).

Minea et al., "Development of a novel recombinant disintegrin, contortrostatin, as an effective anti-tumor and anti-angiogenic agent," Pathophysical Haemost Thromb 34(4-5): 177-183 (2005).

Skolnick et al., "From genes to protein structure and function: novel applications of computational approaches in the genomic era," Trends in Biotech, 18(1):34-39, 2000.

Takeda et al., "Three-dimensional domain architecture of the ADAM family proteinases", Seminars in Cell and Developmental Biology, Academic Press, 20(2):146-152 (2009).

Takeda et al., "Crystal structures of VAP1 reveal ADAMs' MDC domain architecture and its unique C-shaped scaffold," The EMBO Journal 25(11):2388-2396 (2006).

US Advisory Action dated Mar. 18, 2011 for U.S. Appl. No. 11/742,389.

US Interview Summary dated Apr. 8, 2011 for U.S. Appl. No. 11/742,389.

US Notice of Allowance dated Aug. 22, 2012 for U.S. Appl. No. 13/367,267.

US Notice of Allowance dated Apr. 18, 2011 for U.S. Appl. No. 11/742,389.

US Restriction Requirement dated Jan. 26, 2010 for U.S. Appl. No. 11/742,389.

US Final Office Action dated May 2, 2013 for U.S. Appl. No. 13/219,472.

US Office Action dated Jun. 9, 2010 for U.S. Appl. No. 11/742,289.

US Final Office Action dated Dec. 3, 2010 for U.S. Appl. No. 11/742,389.

US Restriction Requirement dated Jul. 12, 2012 for U.S. Appl. No. 13/219,472.

US Restriction Requirement dated Sep. 18, 2009 for U.S. Appl. No. 11/742,389.

US Restriction Requirement dated Jan. 17, 2013 for U.S. Appl. No. 13/201,433.

Yeh et al., "Rhodostomin, A Snake Venom Disintegrin, Inhibits Angiogenesis Elicited by Basic Fibroblast Growth Factor and Suppresses Tumor Growth by a Selective alpha v beta 3 Blockade of Endothelial Cells," Molecular Pharmacology 59(5):1333-1342 (2001).

Davis, A.A. et al. (1994) "A self-renewing multipotential stem cell in embryonic rat cerebral cortex," Nature, 372:263-266.

The Fact Sheet of the Eye Structure, (retrieved from the website http://www.biologymad.com/resources/EyeStructureWS.pdf, on Jun. 30, 2014).

Non-Final Office Action for U.S. Appl. No. 13/201,433, mailed Jul. 1, 2014, 21 pages.

Figure 2

DAPANPCCDAATCKLTTGSQCADGLCCDQCKFMKEGTVCRRARGDLDDYCNGISAGC PRNPFH – contortrostatin ————ECESSFCCRNCKFLNEGTICKRANGDMDDYCNGKTCDC PRNPHKGPAT – echistatin DAPANPCCDAATCKLTTGSQCADGLCCDQCKFMKEGTVCRRARGDLDDYCNGISAGC PRNPHKGPAT – vicrostatin

METHOD OF EXPRESSING PROTEINS WITH DISULFIDE BRIDGES WITH ENHANCED YIELDS AND ACTIVITY

CROSS-REFERENCE TO RELATED APPLICATIONS

This application claims benefit of U.S. Provisional Application No. 61/114,435, filed Nov. 13, 2008, hereby incorporated by reference in its entirety.

FIELD OF INVENTION

The invention relates to methods for expressing proteins with disulfide bridges such as Vicrostatin (VCN), a chimeric variant of native snake venom disintegrin Contortrostatin (CN).

SEQUENCE LISTING

The instant application contains a Sequence Listing which has been submitted via EFS-Web and is hereby incorporated by reference in its entirety. Said ASCII copy, created on Jul. 28, 2011, is named 07540513.txt, and is 12,617 bytes in size.

BACKGROUND OF THE INVENTION

The invention described here relates to an improved method of expressing eukaryotic proteins in prokaryotic hosts, particularly eukaryotic proteins that are required to form multiple disulfide bridges for biological activity. The invention is related to U.S. Publication no. 20060246541 by Minea et al., and titled "Method of expressing proteins with disulfide bridges," incorporated herein by reference including all figures.

A variety of proteins are known which have commercial and medical application and which are characterized in having a complex molecular structure stabilized by disulfide bridging. One such class of the proteins, the disintegrins, include a class of cysteine-rich proteins that are the most potent known soluble ligands of integrins (Gould, Polokoff et al. 1990; Niewiarowski, McLane et al. 1994). The tri-peptide motif RGD (Arg-Gly-Asp) is conserved in most monomeric disintegrins (Niewiarowski, McLane et al. 1994). The RGD sequence is at the tip of a flexible loop, the integrin-binding loop, stabilized by disulfide bonds and protruding from the main body of the peptide chain. Disintegrins bind to the fibrinogen receptor αIIbβ3, which results in the inhibition of fibrinogen-dependent platelet aggregation (Savage, Marzec et al. 1990). Except for barbourin, a KGD-containing disintegrin, which is a relatively specific ligand for αIIbβ3 integrin (Scarborough, Rose et al. 1991), disintegrins are rather nonspecific and can block or disturb the signaling pathways associated with the function of other β3 integrins, as well as β1 integrins (McLane, Marcinkiewicz et al. 1998).

Contortrostatin (CN) is the disintegrin isolated from Agkistrodon contortrix contortrix (southern copperhead) venom (Trikha, Rote et al. 1994). CN displays the classical RGD motif in its integrin-binding loop. Unlike other monomeric disintegrins, CN is a homodimer with a molecular mass (Mr) of 13,505 for the intact molecule and 6,750 for the reduced chains as shown by mass spectrometry (Trikha, Rote et al. 1994).

Receptors of CN identified so far include integrins αIIbβ3, αvβ3, αvβ5, and α5β1 (Trikha, De Clerck et al. 1994; Trikha, Rote et al. 1994; Zhou, Nakada et al. 1999; Zhou, Nakada et al. 2000). Interactions between CN and integrins are all RGD-dependent. As an anti-cancer agent, CN has shown to be a powerful anti-angiogenic and anti-metastatic molecule in in vitro cell-based functional assays and in vivo animal models (Trikha, De Clerck et al. 1994; Trikha, Rote et al. 1994; Schmitmeier, Markland et al. 2000; Zhou, Hu et al. 2000; Markland, Shieh et al. 2001; Swenson, Costa et al. 2004). CN also has the ability to directly engage tumor cells and suppress their growth in a cytostatic manner (Trikha, De Clerck et al. 1994; Trikha, Rote et al. 1994; Schmitmeier, Markland et al. 2000). The antitumoral activity of CN is based on its high affinity interaction with integrins .alpha.5.beta.1, .alpha.v-.beta.3 and .alpha.v.beta.5 on both cancer cells and newly growing vascular endothelial cells (Trikha, De Clerck et al. 1994; Zhou, Nakada et al. 1999; Zhou, Nakada et al. 2000; Zhou, Sherwin et al. 2000). This diverse mechanism of action provides CN with a distinct advantage over many antiangiogenic agents that only block a single angiogenic pathway and/or do not directly target tumor cells.

CN full-length DNA precursor has been cloned and sequenced (Zhou, Hu et al. 2000). CN is produced in the snake venom gland as a multidomain precursor of 2027 bp having a 1449 bp open reading frame (encoding proprotein, metalloproteinase and disintegrin domains), which is proteolytically processed, possibly autocatalytically, to generate mature CN. The CN disintegrin domain encodes 65 amino acids with a molecular weight equal to that of the CN subunit. The CN full-length precursor mRNA sequence can be accessed in the GeneBank database using accession number: AF212305. The nucleotide sequence encoding the 65 amino acid disintegrin domain of CN represents the segment from 1339 to 1533 in the mRNA. Plasmids encoding the CN full-length gene have been described (Zhou, Hu et al. 2000) and are available from the laboratory of Francis S. Markland at University of Southern California.

Structurally, CN is a cysteine-rich protein (10 cysteines per monomer) that displays no secondary structure and, like other disintegrins, has a complex folding pattern that relies on multiple disulfide bonds (four intrachain and two interchain disulfide bonds) to stabilize its tertiary structure (Zhou, Hu et al. 2000). By folding in a compact structure locked by multiple disulfide bonds, CN, like many other venom proteins, has a survival advantage, being less susceptible to a proteolytic attack and better equipped to survive in the harsher extracellular microenvironment. Its highly cross-linked structure and unique biological activity are barriers to producing biologically functional CN (or other disintegrin domain protein) using a recombinant expression system. A further difficulty is that the CN disintegrin domain of the multidomain precursor, from which dimeric CN is derived, displays no secondary structure, a feature that is known to facilitate the proper folding in most nascent proteins (Moiseeva, Swenson et al. 2002). The crystal structure of native CN has not been elucidated. However, the 3-D structure of a closely related heterodimeric disintegrin, acostatin, sharing one chain in common with CN has been determined (Moiseeva, Bau et al. 2008). CN's folding pattern is presumably as complex as other viperid dimeric disintegrins that have been studied (Calvete, Jurgens et al. 2000; Bilgrami, Tomar et al. 2004). Attempts to express snake venom disintegrins such as CN as functional native conformers and at a high level of expression suitable for mass production in eukaryotic and prokaryotic systems have been so far disappointing (e.g., see (Moura-da-Silva, Linica et al. 1999).

U.S. Publication no. 20060246541 describes the expression of a chimeric snake venom disintegrin Vicrostatin (VCN) in the Origami B (DE3)/pET32a system. Unlike other E. coli strains, the Origami B is unique in that, by carrying mutations in two key genes, thioredoxin reductase (trxB) and glutathione reductase (gor), that are critically involved in the control of the two major oxido-reductive pathways in *E. coli*, this bacterium cytoplasmic microenvironment is artificially shifted to a more oxidative redox state, which is the catalyst state for disulfide bridge formation in proteins (Bessette et al., 1999; Prinz, et al. 1997).

The Origami B strain has growth rates and biomass yields similar to those obtained with wild-type *E. coli* strains, which makes it an attractive and scalable production alternative for difficult-to-express recombinant proteins like VCN. This strain is also derived from a lacZY mutant of BL21. The lacY1 deletion mutants of BL21 (the original Tuner strains) enable adjustable levels of protein expression by all cells in culture. The lac permease (lacY1) mutation allows uniform entry of IPTG (a lactose derivative) into all cells in the population, which produces a controlled, more homogenous induction. By adjusting the concentration of IPTG, the expression of target proteins can be optimized and theoretically maximal levels could be achieved at significantly lower levels of IPTG. Thus the Origami B combines the desirable characteristics of BL21 (deficient in ompT and lon proteases), Tuner (lacZY mutant) and Origami (trxB/gor mutant) hosts in one strain. As mentioned above, the mutations in both the thioredoxin reductase (trxB) and glutathione reductase (gor) greatly promote disulfide bond formation in the cytoplasm (Prinz, et al. 1997).

In U.S. Publication no. 20060246541, it was shown that VCN, a chimeric disintegrin construct that was generated by genetically fusing the C-terminal tail of a viperid short-sized disintegrin, Echistatin, to the crotalid disintegrin, Contortrostatin, could be produced recombinantly in an active soluble form in Origami B (DE3) with an yield of 10-20 mg active product per liter of bacterial culture. In such a system, VCN was generated as a fusion protein with bacterial thioredoxin A (TrxA) using an expression method previously described (LaVallie, et al., 1993). As shown below, however, this expression system will not produce soluble and/or active product in every case. It is therefore desirable to include changes to production methods that expand the types of molecules that can be produced as soluble and/or active product as well as to enhance fusion protein production yield.

SUMMARY OF THE INVENTION

The present invention is based on the discovery of a more efficient natural selection process for, as an example, expression of a chimeric snake venom disintegrin Vicrostatin (VCN) in the Origami B (DE3)/pET32a system, wherein the instant method significantly increases the likelihood of generating increased amounts of correctly-folded active conformers of proteins with disulfide bridges (such as VCN). This can be achieved by growing Origami B cells in a less selective environment and thus allowing for the generation and expansion of VCN-transformants that display a more optimal redox environment during the induction of the heterologous recombinant protein production. The invention further provides methods useful for expressing non-procaryotic biologically active disulfide-rich protein in prokaryotic host cells.

Accordingly, in one aspect, the invention provides a method of expressing non-procaryotic biologically active disulfide-rich protein in prokaryotic host cells said method comprising a) obtaining a prokaryotic host cell transformed with an expression vector encoding a fusion protein under inducible control, said fusion protein comprising an N-terminal segment encoding thioredoxin and a C-terminal segment encoding said disulfide rich protein, wherein said host also carries stable mutations in thioredoxin reductase B (trxB) gene and/or the glutathione reductase (gor) gene, wherein said expression vector has an antibiotic resistance gene which makes it selectable on a first antibiotic, and wherein said trxB and gor mutations are selectable on at least one additional antibiotic to maintain the expression vector and trxB and gor mutations in said host cells during growth; b) growing the host cells of step a) in the presence of the first and said at least one additional antibiotic to obtain a sufficient number of cells suitable to seed a reactor in which host cells will be grown and the fusion protein expression induced; and c) seeding the reactor with the cells of step b) and growing the cells and inducing expression of the fusion protein, wherein said cells in the reactor are grown in the presence of the first antibiotic and in the absence of said at least one additional antibiotic.

In other aspects, the host cells express mutant products of both the trxB and gor genes, the host cells are mutant in both trxB and gor genes, the trxB and gor genes are selectable on different antibiotics, and/or the host cells are deficient in any one or more of ompT or ion gene products.

In another aspect, the thioredoxin portion of the fusion protein comprises the sequence of SEQ ID NO: 1.

In other aspects, the fusion protein comprising an N-terminal segment encoding thioredoxin and a C-terminal segment encoding the disulfide rich protein further comprises a sequence encoding a cleavage site located between the sequence encoding thioredoxin and the sequence encoding the disulfide rich protein, or the fusion protein further includes a peptide sequence which is a ligand for a receptor.

In another aspect, the reactor is a fermentation vessel.

In another aspect, the prokaryotic host cell is a bacterial host cell and in yet another aspect, the bacterial host cell is an Origami strain.

In another aspect, the method of expressing non-procaryotic biologically active disulfide-rich protein in prokaryotic host cells wherein following step c, the cells are harvested and processed to obtain a purified preparation of said biologically active disulfide rich protein.

In another aspect, the biologically active disulfide rich protein is Vicrostatin (VCN), comprising the amino acid sequence shown in FIG. 1. In another aspect, VCN is expressed as a monomer. And in yet another aspect, the biologically active VCN is at least 50% pure, more preferably at least 60% pure, more preferably at least 70% pure, more preferably at least 80% pure, more preferably at least 90% pure, more preferably at least 99% pure and most preferably 100% pure.

In other aspects, the biologically active VCN is capable of: inhibiting cell migration, such as HUVEC, MDA-MB-231 or MDA-MB-435 cells, such as through a reconstituted basement membrane; increasing the level of phosphorylation of FAK, such as in MDA-MB-435 cells; inducing apoptosis, such as in HUVEC in culture; and/or inhibiting endothelial tube formation, such as in HUVECs in culture.

BRIEF DESCRIPTION OF THE FIGURES

FIG. 2 shows a comparison between native CN, recombinant VCN and Echistatin amino acid sequences. Regions corresponding to the integrin binding loop (underline) and C-terminal tail (double underline) are shown.

DETAILED DESCRIPTION OF THE INVENTION

Figure 1:
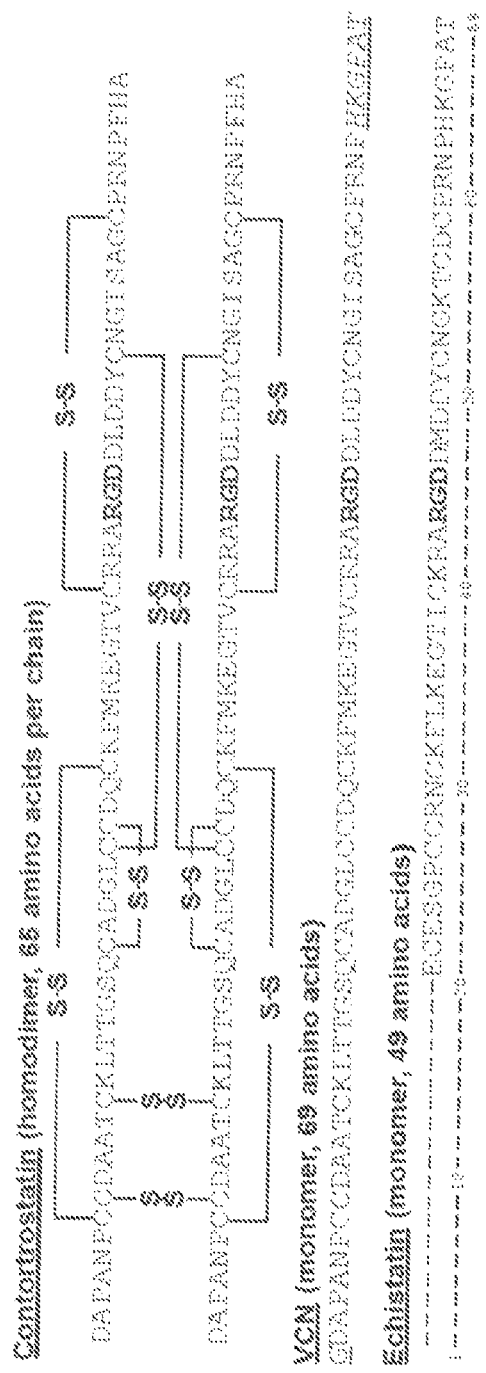
FIG. 1 shows a comparison between native CN, recombinant VCN and Echistatin amino acid sequences. The Arg-Gly-Asp tripeptide motif is depicted in bold whereas VCN's N-terminal extra residue and C-terminal graft are italicized and underlined.

This method improves upon the expression system disclosed in U.S. Publication no. 20060246541 which includes, as an embodiment, expression of a chimeric snake venom disintegrin Vicrostatin (VCN) in the Origami B (DE3)/pET32a system. Through what is believed a more efficient natural selection process, the instant method significantly increases the likelihood of generating increased amounts of correctly-folded active conformers of proteins with disulfide bridges (such as VCN). This is achieved by growing Origami B cells in a less selective environment and thus allowing for the generation and expansion of VCN-transformants that display a more optimal redox environment during the induction of the heterologous recombinant protein production.

The expressed non-procaryotic protein can be "disulfide rich." As used herein, "disulfide rich" refers to a protein that has at least two or more disulfide bridges. A disulfide rich protein can have at least 2, 3, 4, 5, 6, 7, 8, 9, or 10 disulfide bridges.

The expressed non-procaryotic protein can be a fusion to a thioredoxin. As used herein, "thioredoxin" refers to a family of small (about 13 kD) electron carrier proteins with a dithiol/disulfide active site (CGPC), which are the major cellular protein disulfide reductases which serve as electron donors for enzymes such as ribonucleotide reductases, thioredoxin peroxidases (peroxiredoxins) and methionine sulfoxide reductases. In bacteria, the redox potential of thioredoxin is maintained by thioredoxin reductase (thioredoxin B, TrxB).

As used herein, thioredoxin refers to class of small proteins (about 10-12 kD) that contain a short sequence motif that includes a Cys-X1-X2-Cys sequence (the active site) and an overall structure containing this motif that corresponds to what is called a thioredoxin-like fold (Martin 1995). The cysteine pair at the ends of this motif may oxidize to form a disulfide bond which is reduced by the NADPH-dependent enzyme thioredoxin reductase. An exemplary thioredoxin is thioredoxin A (TrxA) from *E. coli*, which is about 109 amino acids in length and is encoded by the trxA gene. The amino acid sequence of *E. coli* wild type thioredoxin A is shown below with the active site CXXC bolded and underlined, (SEQ ID NO: 1)
MSDKIIHLTDDSFDTDVLKADGAILVDFWAEWCGPC

KMIAPILDEIADEYQGKLTVAKLNIDQNPGTAPKYG

IRGIPTLLLFKNGEVAATKVGALSKGQLKEF LDANLA.

Active site mutants of thioredoxin may be used in place of wild type thioredoxin in the fusion protein. Thus, thioredoxin active-site motif CXXC can be replaced with an active-site motif from another oxido-reductase. For example, active site mutants of wild type thioredoxin A may be used in place of wild type thioredoxin in the fusion construct with the eukaryotic protein. In this regard, thioredoxin A's active site motif CGPC may be replaced with the active site motif CPYC, taken from another bacterial oxido-reductase, glutaredoxin A (also called glutaredoxin 1). This mutant may be referred to as a glutaredoxin-like thioredoxin. Another thioredoxin active site mutant is the PDI-like thioredoxin, generated by replacing the active site wild type motif CGPC with the active site motif CGHC, taken from eukaryotic protein disulfide isomerase (PDI).

In addition to full-length thioredoxin A, shorter segments may be used as the fusion with the eukaryotic protein.

Thioredoxin that is used in the fusion protein can be from the same type of host that is to be used for expression. For example, the encoded thioredoxin portion of the fusion protein is preferably from a particular bacterial host if that particular bacterial host is contemplated as the expression host.

Eukaryotic proteins that may be expressed by the methods herein encompass a wide range of disulfide bridge-containing proteins including monomeric and multimeric disintegrins, snake venom toxins (PI, PII or PIII class), antibody fragments (in scFv, Fab, or F(ab')2 formats), cytokines, chemokines, interferons, tumor growth factors, scorpion toxins, conotoxins, various domains of ADAM (A Disintegrin and A Metalloprotease) proteins, vaccines, growth factors, plasminogen activators, and combinations of the afore-mentioned proteins belonging to different classes and expressed as fusion proteins (for example a chemokine fused to a disintegrin etc), as well as other bio-active eukaryotic cysteine-rich proteins (e.g. jararhagin-C—GeneBank accession number AAB30855; disintegrin schistatin—GeneBank accession number P83658; snake metalloproteinase fibrolase—GeneBank accession number P83255; human interleukin-2 precursor—GeneBank accession number NP000577; human interferon-γ—GeneBank accession number NP00610; human transforming growth factor, β2—GeneBank accession number NP003229; human liver expression chemokine, CCL16—GeneBank accession number O15467; omega-conotoxin CVID precursor—GeneBank accession number P58920; scorpion chlorotoxin—GeneBank accession number P45639; human ADAM 9 precursor—GeneBank accession number Q13443; human vascular endothelial factor A, VEGF-A—GeneBank accession number P15692; human tissue-type plasminogen activator precursor, t-PA—GeneBank accession number P00750) etc.

As used herein "ADAM" (a disintegrin and a metalloprotease) is a family of transmembrane eukaryotic proteins that contain several different domains including a disintegrin domain and a metalloprotease domain.

As used herein, "disintegrin" refers to a class of cysteine-rich proteins that are potent soluble ligands of integrins and which are involved in regulating many processes such as cell-cell and cell-extracellular matrix adhesion, migration and invasion, cell cycle progression, differentiation and cell type specification during development of many metazoan organisms, and cell death and apoptosis. The tri-peptide motif RGD (Arg-Gly-Asp) is conserved in most monomeric disintegrins and is located at the tip of a flexible loop, the integrin-binding loop, which is stabilized by disulfide bonds and protruding from the main body of the peptide chain. All disintegrins purified from snake venoms bind to the fibrinogen receptor, integrin αIIbβ3, the binding of which results in the inhibition of fibrinogen-dependent platelet aggregation. Most disintegrins also bind to integrins αvβ3 (a vitronectin receptor) and α5β1 (a fibronectin receptor) in an RGD-dependent manner.

As used herein, "contortrostatin" (CN) refers to a disintegrin isolated from Agkistrodon contortrix contortrix (southern copperhead) venom (Trikha, Rote et al. 1994). CN is produced in the snake venom gland as a multidomain precursor of 2027 bp having a 1449 bp open reading frame encoding the proprotein, metalloproteinase and disintegrin domains. The precursor is proteolytically processed, possibly autocatalytically, to generate mature CN. The full length CN preprotein is encoded by the nucleotide sequence 85-1536 of the full length mRNA (GeneBank AF212305), whereas the disintegrin domain of CN represents 1339-1533 of the mRNA. The CN disintegrin domain, which contains 65 amino acids, is shown below with the RGD sequence underlined.

(SEQ ID NO: 2)
DAPANPCCDAATCKLTTGSQCADGLCCDQCKFMKEG

TVCRRA<u>RGD</u>DLDDYCNGISAGCPRNPFH.

The sequence HKGPAT, which represents the C-terminal amino acid sequence of the monomeric disintegrin, echistatin, was included at the C-terminal end of the CN disintegrin domain sequence. This construct is a chimera that combines by the means of genetic engineering the sequences of two snake venom disintegrins with different origins: echistatin (a viperid disintegrin) and contortrostatin (a crotalid disintegrin). For this reason, this disintegrin construct that carries a C-terminal graft is referred to as "Vicrostatin" or "VCN." CN disintegrin domain without the HKGPAT sequence is referred to as "rCN" or "rCN construct." The amino acid sequence of vicrostatin is shown below as SEQ ID NO: 3.

```
                                            (SEQ ID NO: 3)
    DAPANPCCDAATCKLTTGSQCADGLCCDQCKFMKEG

TVCRRARGDDLDDYCNGISAGCPRNPFHHKGPAT
```

A comparison of CN, VCN, and Echistatin amino acid sequences is shown in FIG. 1. Crystallographic data showed that CN is a dimer with two identical chains configured in an antiparallel fashion. Unlike CN, mass spectrometry data shows that VCN is a monomer.

As shown in FIG. 1, Contortrostatin can form up to at least ten disulfide bridges, both intermolecular as well as intramolecular for the dimer.

The integrin binding loop and the C-terminal tail are important features of the disintegrin domain. FIG. 2 shows an alignment of the disintegrin domains for CN, VCN and Echistatin. Echistatin is a special case of a disintegrin domain being naturally truncated at the N-terminus. Accordingly, the integrin binding loop (underlined) and the C-terminal tail (double underlined) are located within the disintegrin domain. From a functional standpoint (i.e., the ability of a disintegrin domain to engage integrin receptors) the length of the N-terminus of the disintegrin domains is not important. The folding of the integrin binding loop is related to activity. Aside from Echistatin, the 13-aa integrin binding loop is found in the C-terminal half of CN as well as in the vast majority of disintegrins isolated from snake venoms. In addition to the integrin binding loop, another structural element is the C-terminal tail (double underlined), which can fold with the integring binding loop and can also participate in integrin binding. The VCN sequence was created by swapping CN's C-terminal tail with Echistatin's.

Host cells transformed with the expression vector encoding the thioredoxin/eukaryotic protein are cultured to produce the fusion protein containing the eukaryotic protein in biologically active form. The expressed protein may be obtained directly from cells in a soluble form by routine cell lysis methods, from which it can be isolated in substantially pure form by routine purification methods.

As used herein, the term "purified" in reference to polypeptides (or proteins) does not require absolute purity. Instead, it represents an indication that the polypeptide(s) of interest is(are) in an environment in which the protein is more abundant (on a mass basis) than the environment from which the protein was initially produced. Purified polypeptides may be obtained by a number of methods including, for example, chromatography, preparative electrophoresis, centrifugation, precipitation, affinity purification, etc. The degree of purity is preferably at least 10%. One or more "substantially purified" polypeptides are at least 50% of the protein content of the environment, more preferably at least 75% of the protein content of the environment, and most preferably at least 95% of the protein content of the environment. Protein content may be determined, for example, using a modification of the method of Lowry et al. (Lowry, Rosebrough et al. 1951), described by Hartree (Hartree 1972), using bovine serum albumin as a protein standard.

In accordance with the methods herein, a cleavage site may be designed between the N-terminal thioredoxin sequence and the C-terminal containing the eukaryotic protein sequence in order to obtain the eukaryotic protein free from thioredoxin. The fusion protein may be purified prior to any cleavage step. Any number of well known cleavage sites may be used for this purpose. A suitable protease cleavage site is the TEV protease cleavage site, which comprises the amino acid sequence ENLYFQG/S (three letter code: Glu-Asn-Leu-Tyr-Phe-Gln-Gly/Ser). The TEV site may be engineered just upstream of the N-terminus of the disulfide containing eukaryotic protein. A chemical cleavage site also may be used for this purpose. For example, a DP (Asp-Pro) dipeptide sequence can be engineered in a similar location to that of the TEV site in the fusion protein. Formic acid hydrolysis can then be used to cleave the protein at the DP site.

In some embodiments, the construct consists of a thioredoxin fused to the eukaryotic protein and a "tag" sequence to assist in detection of the fusion protein or in purification of the fusion protein or in purification of the eukaryotic protein following expression. A tag sequence can be a His-tag or poly His sequence or any sequence of amino acids that can coordinate a metal ion. The tag sequence also can be any part of a ligand/receptor binding relationship (e.g. antibody and peptide antigen). The tag sequence may be engineered into the fusion protein at the N-terminus, C-terminus or anywhere in between as dictated by constraints on the function of the expression system and the eukaryotic protein. The tag sequence is preferably upstream of any cleavage site in the fusion protein.

In accordance with the invention methods, sequence encoding the fusion protein is contained within a suitable expression vector under control of appropriate regulatory control sequences such as a promoter, optional enhancer, repressor, and the like. Suitable expression vectors for foreign protein expression in a microbial host are well known in the art. In one embodiment, the vector is pET32a. In another embodiment the vector is the pET32a/pCDFDuet-1 combination.

In another embodiment, bacterial host cells may be engineered to cytoplasmically express a disulfide isomerase normally targeted to the periplasmic space of the host. In one embodiment, the disulfide isomerase is DsbC. As used herein, "disulfide isomerase" refers to a prokaryotic protein which rearranges incorrect disulfide bonds during oxidative protein folding. DsbC is specifically activated by the periplasmic N-terminal domain (DsbD .alpha.-domain) of the transmembrane electron transporter DsbD. In the bacterial periplasm, the formation of protein disulfide bonds is catalyzed by DsbA and DsbC. DsbA is a monomer that is maintained in a fully oxidized state by the membrane enzyme DsbB, whereas DsbC is a dimer that is kept reduced by a different membrane protein, DsbD. Although the catalytic regions of DsbA and DsbC are composed of structurally homologous thioredoxin motif domains, DsbA serves only as an oxidase in vivo, whereas DsbC catalyzes disulfide reduction and isomerization and also exhibits significant chaperone activity.

Cytoplasmic localization of DsbC can be achieved by expressing the mature protein without a signal sequence. The sequence of E. coli DsbC is shown below without the signal sequence and with the active site CGYC underlined and bolded.

```
                                            (SEQ ID NO: 4)
    DDAAIQQTLAKMGIKSSDIQPAPVAGMKTVLTNSGV

LYITDDGKHIIQGPMYDVSGTAPVCNVTNKMLLKQLN

ALEKEMIVYKAPQEKHVITVFTDITCGYCHKLHEQM

ADYNALGITVRYLAFPRQGLDSDAEKEMKAIWCAKD
```

```
                              -continued
            KNKAFDDVMAGKSVAPASCDVDIADHYALGVQLGVS

GTPAVVLSNGTLVPGYQPPKEMKEFXDEHQKMTSGK
```

In further embodiments, active site mutants of the disulfide isomerase with increased isomerase activity can be used in place of the wild type sequence. For example, the DsbC active site CGYC can be replaced with CGFC or CTFC for greater isomerase activity. Expression of signal sequenceless DsbC (or active site mutants) may be employed in host cells that are trxB and/or gor deficient. Double-mutant strain FA113 and its derivatives with both trxB and gor mutations can be used for this purpose.

In another embodiment, the host cells can be engineered to cytoplasmically express the α-domain of bacterial thiol-disulfide interchange protein DsbD (DsbD α-domain). As used herein, "DsbD" is a transmembrane *E. coli* enzyme that is normally targeted to the inner periplasmic membrane, with the α-domain facing the periplasmic space where it acts as a disulfide interchange catalyst (redox catalyst). Cytoplasmic localization of DsbD is achieved by expressing the domain without any signal sequence. Expression of the DsbD α-domain cytoplasmically may be combined with host cells which are trxB and/or gor deficient and which may express DsbC (signal-sequenceless wild type enzyme or an active site mutant). The DsbD α-domain represents the first 132 amino acids of mature DsbD from which a cleavable signal sequence of 19 aa is removed. The sequence of the DsbD α-domain without the leader sequence and with the catalytic site underlined is shown below.

```
                                          (SEQ ID NO: 5)
            GLFDAPGRSQFVPADQAFAFDFQQNQHDLNLTWQIK

DGYYLYRKQIRITPEHAKIADVQLPQGVWHEDEFYG

KSEIYRDRLTLPVTINQASAGATLTVTYQGCADAGF

CYPPETKTVPLSEVVANNEASQPV
```

The DsbD α-domain without its leader sequence is designated AssDsbD α-domain. Host cells may be modified to cytoplasmically express DsbC and the α-domain of the DsbD.

In another embodiment, host cells are modified to be deficient in thioredoxin reductase and/or glutathione reductase activity. Thioredoxin reductase (thioredoxin B, TrxB) is a key *E. coli* enzyme that controls the first of the two major reductive pathways in the cytosol. A deficiency in thioredoxin reductase can be achieved by expressing a transdominant negative mutant product of the trxB gene from a separate plasmid in host's cytoplasm. Glutathione reductase (Gor) is another key enzyme that controls the second major reductive pathway in the cytosol. A deficiency in glutathione reductase can be achieved by expression of a transdominant negative mutant product of the gor gene from the same or a separate plasmid in host's cytoplasm. These mutations may be used together or alone and may be combined with any other host cells variations described herein.

In a further embodiment, host cells are deficient in one or more proteases. Exemplary such proteases include those encoded by ompT and lon genes. For example, *E. coli* host cells AD494(DE3)pLysS are deficient in trxB gene as well as ompT and lon gene products. *E. coli* strain Origami B(DE3) pLysS and Rosetta-gami B(DE3)pLysS are deficient in trxB, gor, ompT and lon gene products. These mutations may be used in combination with any other host cells variations described herein. Thus, the ompT and lon mutations may be used in combination with host cells deficient in trxB and/or gor as well as host cells modified to cytoplasmically express DsbC (wild type protein or active site mutant) and/or the DsbD .alpha.-domain.

Disulfide Bond Formation in the *E. coli* Cytoplasm and Thioredoxins

Bacterial cytoplasmic proteins do not generally contain structural disulfide bonds, although certain cytoplasmic enzymes form such bonds as part of their catalytic cycles. The disulfide bonds in these latter enzymes are reduced in *E. coli* cytoplasm by two systems: the thioredoxin pathway and the glutathione/glutaredoxin pathway (Stewart, Aslund et al. 1998). Under physiological conditions, these two reductive pathways maintain the cytoplasm in a reduced state that strongly disfavors the formation of stable disulfide bonds in proteins. Tthioredoxin reductase (encoded by trxB gene) and glutathione reductase (encoded by gor gene) as the key enzymes. However, mutants in which the reduction of one or both thioredoxins and glutathione is impaired (trxB or trxB/gor mutants) accumulate oxidized disulfide bond proteins, like enzymatically active human alkaline phosphatase in the cytoplasm (Stewart, Aslund et al. 1998; Bessette, Aslund et al. 1999). The formation of disulfide bond in these mutants is dependent on the presence of cytoplasmic thioredoxins that suffer a role reversal and actively assist the formation of disulfide bridges, thus functioning as oxidases in this case. The double mutants grow very poorly in the absence of an exogenous reductant (e.g. DTT) and accumulate extragenic suppressors at a high frequency: fast growing colonies that are DTT-independent. This suppressor mutation was mapped in ahpC gene, which encodes for a peroxiredoxin in its wild type form. The mutation borne by FA113 (one of the fast growing suppressors) makes this enzyme act as a disulfide reductase (Jurado, Ritz et al. 2002). In rich or defined media, *E. coli* FA113 grows almost as well as *E. coli* DHB4 with doubling times of approx. 35 minutes. A delay in the growth-rate of FA113 (doubling times of approx. 60 minutes) has been reported when some antibiotics such as chloramphenicol, kanamycin, or tetracycline were used for selection (Jurado, Ritz et al. 2002).

Prokaryotic System for Supporting Disulfide Bond Formation of Heterologous Proteins in Cytoplasm In the quest to further engineer the FA113 double mutant to make it more efficient in its ability to assist the correct folding of disulfide-rich proteins in cytoplasm, the activity of the periplasmic enzymatic equipment is imported into the cytoplasm to help the folding of heterologous recombinant proteins in this compartment. Previous descriptions of this approach have focused on heterologous proteins such as antibody fragments (in scFv or Fab format) or some other eukaryotic cysteine-rich proteins (Levy, Weiss et al. 2001; Jurado, Ritz et al. 2002; Venturi, Seifert et al. 2002; Maskos, Huber-Wunderlich et al. 2003).

Modified expression hosts reported previously contain either a signal sequenceless oxidase (ΔssDsbA or active site mutated variants) or a signal sequenceless isomerase (usually ΔssDsbC) imported from the periplasmic space and simultaneously co-overexpressed, along with the cysteine-rich recombinant protein, in the cytoplasm of the double mutant trxB⁻/gor⁻ strain (Levy, Weiss et al. 2001; Jurado, Ritz et al. 2002). This type of system has been used to generate Fab antibody fragments in *E. coli*, and has been shown to improve the yield of correctly folded antibodies compared to wild type strains (from nanograms to approx. 1 mg/L of recombinant protein). However, although considered as a step forward, such system failed to generate the yields expected. One problem with this approach is the oxidase/isomerase combination simultaneously co-overexpressed does not efficiently catalyze the disulfide bridge formation in the recombinant protein because such system lacks the extraordinary ability of the periplasmic space to regenerate its foldases. Based on the periplasmic space principle, the oxidase and the isomerase imported from the periplasmic space need be constantly recharged in order to function. For this reason, a third component is required to bridge the oxidase/isomerase enzymatic equipment imported into the cytoplasm. This component(s) should link the oxidase with the isomerase co-overexpressed in FA113 by recharging them constantly and keeping the flow of reducing equivalents in one direction, and disulfide bridge transfer in the other direction.

In accordance with the methods of the invention, an embodiment including the recombinant system uses key enzymes from both compartments (periplasmic and cytoplasmic) that are naturally interacting with each other, instead of molecules that are forced to artificially interact to reconstitute the system. A natural combination includes DsbA, DsbB, DsbC and DsbD, but to import all of them into the cytoplasm is difficult. Simultaneous co-overexpression in the cytoplasm of DsbA, DsbB, DsbC and DsbD has been reported. However the net gain from such expression was not impressive (DsbA/DsbB/DsbC/DsbD expression plasmid—CA2281035). This may be explained by the fact that DsbB and DsbD which physiologically function as membrane-embedded molecules might not function properly when expressed as soluble proteins in the bacterial cytoplasm. Second, DsbB, as described above, is coupled with the electron transfer chains. By expressing DsbB in the cytoplasm, the protein may be unable to recharge DsbA, compromising the expression system. On the other hand, the DsbC-DsbD partnership might not be affected assuming that the soluble form of DsbD can still function in the cytoplasm and react with thioredoxin, its upstream partner, and with DsbC, its downstream partner. For a system designed on DsbC-DsbD partnership in the cytoplasm to further become auto-regenerating, it would also need a third component—an oxidase partner. The idea of using cytoplasmic thioredoxin A (thioredoxin 1) as DsbC-DsbD oxidase partner is attractive because DsbD naturally interacts with both thioredoxin A and DsbC.

DsbD molecule is a large transmembrane protein displaying hydrophobic domains. Because of its size and membrane spanning hydrophobic β-domain, expression of the DsbD α-domain in the cytoplasm is preferred over expression of the full length DsbD molecule. The full-length DsbD protein is too big to be efficiently co-overexpressed in the same system with three other proteins. The DsbD α-domain represents amino acids 1-131 of DsbD following removal of a cleavable signal sequence of 19 aa. DsbD α-domain on its own interacts efficiently with DsbC in vitro, and is able to keep it reduced and to subsequently recharge its isomerase partner (Goldstone, Haebel et al. 2001; Goulding, Sawaya et al. 2002). When stoichiometric amounts of reduced DsbD α-domain and oxidized DsbC are mixed, a rapid reaction takes place and DsbC is very quickly reduced. Whether DsbD α-domain interacts with thioredoxin A, the natural partner of DsbD, has been suggested by Collet et al (Collet, Riemer et al. 2002), who describes an in vitro reconstituted periplasmic bacterial disulfide isomerization system. First, in the presence of a catalytic amount of DsbD α-domain alone, the reduction of DsbC took place at a rate comparable to that measured in the presence of all three domains together. This indicates that the activity observed in the presence of all three domains could only be explained by the contribution of the .alpha.-domain alone. Second, by mixing stoichiometric quantities of thioredoxin with DsbD α-domain, it was surprisingly found that thioredoxin efficiently reduces α-domain directly in vitro. A very low activity was observed when thioredoxin was incubated with oxidized DsbD γ-domain or with oxidized DsbC. This last observation is significant because it is known that DsbC is kinetically isolated from the oxidation system (periplasmic DsbA), and that DsbC does not interact with cytoplasmic thioredoxin either.

As disclosed herein, a novel powerful redox system can be recreated in the cytoplasm of $E.\ coli$ trxB$^-$/gor$^-$ double-mutant strain (FA113) by combining an oxidase (thioredoxin A) with an isomerase (ΔssDsbC; mature DsbC minus the signal sequence) and further linking them together in the same compartment by utilizing the DsbD α-domain (ΔssDsbDα), the missing molecular component with the ability to regenerate the foldase enzymatic equipment. In this novel in vivo system, the recombinant disulfide containing eukaryotic protein closes the circuit and DsbD α-domain is the key molecule to fill the gap between the oxidation and isomerization pathways ensuring that the reducing equivalents from thioredoxin to DsbC are flowing in one direction, while the constant transfer of disulfide bridges is taking place in the other direction.

Attempts to mutate the active sites of thioredoxin and DsbC to increase the activity of these enzymes have been reported. (Mossner, Huber-Wunderlich et al. 1998; Bessette, Aslund et al. 1999; Bessette, Qiu et al. 2001). The wild type thioredoxin has an active site with a very low redox potential (−270 mV), a value that is in good agreement with its primary function as a reductase in bacteria. It was reported that improved oxidase activity of thioredoxin A can be achieved by replacing the wild type thioredoxin active site motif CGPC with bacterial glutaredoxin A's active site motif CPYC. Such change modifies the active site redox potential of thioredoxin from −270 mV (wild type) to −195 mV (glutaredoxin-type), and the mutated glutaredoxin-type thioredoxin becomes a better oxidase. The glutaredoxin-type mutant was able to generate better yields of disulfide-rich proteins when this thioredoxin mutant and the disulfide rich proteins were co-overexpressed in the same system (Bessette, Aslund et al. 1999).

Another thioredoxin mutant of interest is the PDI-like thioredoxin, a thioredoxin including the eukaryotic protein disulfide isomerase active site motif. It has been previously shown that replacing the wild type thioredoxin active site motif with the eukaryotic protein disulfide isomerase sequence CGHC increases the active site redox potential from −270 mV to approximately −229 mV. The change in redox potential renders the PDI-type thioredoxin a more effective enzyme in the FA113 system, not only a better oxidase than wild type thioredoxin but also a better reductase than the glutaredoxin-type thioredoxin mutant.

Active site mutants of DsbC have also been described. The DsbC active site CGYC was replaced with CGFC or CTFC which were found to increase isomerase activity. The yield of a multiple disulfide-bond protein generated in the FA113 strain has been shown to increase when these active site DsbC mutants were co-overexpressed (Bessette, Qiu et al. 2001).

Origami and Rosetta-gami strains are double-mutants in trxB and gor gene products that render the two main reducing enzymatic pathways in $E.\ coli$ cytoplasm inoperable. This makes the cytoplasmic microenvironment more oxidative which, ultimately, makes this compartment a more suitable place for disulfide bond formation.

The Origami and Rosetta-gami strains have growth rates and biomass yields close to those obtained by $E.\ coli$ wild type strains, making it attractive for large-scale production and purification of recombinant CN.

For recombinant production of CN in *E. coli*, a system consisting of Origami B(DE3)pLysS expression host in combination with pET32a vector with a strong T7lac promoter (Novagen) has been employed. Origami B host strains carry the same trxB/gor mutations as the original Origami strains (FA113), except that they are derived from a lacZY mutant of BL21. Thus, the Origami B strains combine the desirable characteristics of BL21 (deficient in ompT and lon proteases), Tuner and Origami hosts into a single strain.

It has been found that mutations in both the thioredoxin reductase (trxB) and glutathione reductase (gor) genes greatly promote disulfide bond formation in the cytoplasm. Expression in Origami (DE3) yields 10-fold more active protein than in another host even though overall expression levels are similar (Prinz, Aslund et al. 1997).

In the absence of IPTG (isopropyl-beta-D-thiogalactopyranoside) inducer, there is a detectable level of expression of T7 RNA polymerase from the lacUV5 promoter in the DE3 lysogens, resulting in a basal expression of the recombinant protein. Such low level of recombinant protein expression in *E. coli* may interfere with the normal growth processes of the cell and may, therefore, be "toxic" to the bacteria. One approach to control basal expression is to use vectors that contain a T7lac promoter (Studier, Rosenberg et al. 1990; Dubendorff and Studier 1991). These plasmids contain a lac operator sequence just downstream of the T7 promoter and carry the natural promoter and coding sequence for the lac repressor (lace, oriented so that the T7lac and lad promoters diverge. The lac repressor in the vector acts both at the lacUV5 promoter level in the host chromosome to repress transcription of T7RNA polymerase gene by the host polymerase and at the T7lac promoter in the vector to block transcription of the eukaryotic gene by any T7RNA polymerase that is produced.

Reducing basal eukaryotic protein expression may be accomplished by expressing in host strains that contain a compatible chloramphenicol-resistance plasmid from which is expressed a small amount of T7 lysozyme, a natural inhibitor of T7RNA polymerase (Studier 1991). A pLysS host has little effect on growth rate and overall pLysS increases the tolerance of λDE3 lysogens for plasmids with toxic inserts: Unstable plasmids become stable, and plasmids that would not otherwise be established can be maintained and expressed. The presence of pLysS has the further advantage of facilitating the preparation of cell extracts because cells are less resistant to freezing and thawing cycles and lyse easily.

The Tuner strain and derivatives (Origami B and Rosetta-gami B) are lacY1 deletion mutants of BL21 that enable adjustable levels of protein expression. The lac permease (lacY1) mutation allows a uniform entry of IPTG (a lactose derivative) into the cell, which produces a concentration-dependant, homogenous level of induction. By adjusting the concentration of IPTG, expression can be regulated from a very low up to high levels; however the optimal level of eukaryotic protein expression may be achieved at a significantly lower level of IPTG than is normally used. This approach offers cost savings with respect to IPTG.

An important feature of the Origami and Rosetta-gami strains is the ability to provide sufficient oxidizing power to catalyze disulfide bond formation of heterologous recombinant proteins. However, such a system lacks isomerization power. Disulfide bond formation of recombinant proteins takes place at an accelerated rate in Origami/Rosetta-gami cytoplasm compared to wild type *E. coli*, but there is no enzymatic equipment to ensure the correct match and to generate a product with identical disulfide pattern as in the native conformers.

Disulfide bond isomerization, and not disulfide bond formation, is limiting for folding of multiple disulfide-bond proteins in the periplasm of *E. coli* wild type cells. Origami cells have no enzymatic equipment in the cytoplasm to either ensure the correct pairing of disulfide bridges or to reshuffle the incorrectly formed ones into the correct position. Thus, further engineering of the host protein may be needed to increase the level of isomerization activity in the cytoplasm.

Origami *E. coli* strain (FA113) may be modified to cytoplasmically overexpress the DsbC isomerase (DsbC without its signal sequence; "ΔssDsbC") and the DsbD α-domain (DsbD without a signal sequence; "ΔssDsbDα"), the latter functioning to reduce cysteines of the active site of DsbC isomerase. Although not wishing to be bound by any theory, it is believed that DsbD α-domain is the key molecule to fill the gap between the novel oxidation (TrxA) and isomerization (DsbC) pathways in the cytoplasm that keeps the reducing equivalents from thioredoxin to DsbC flowing in one direction and the constant transfer of disulfide bridges in the other direction. The combination of these two features creates a system with the capacity for auto-regeneration.

Increased expression of disulfide-bridge containing proteins may be obtained by using mutant trxA and dsbC gene products. Active site mutants with increased oxidase and isomerase activity have been reported (Mossner, Huber-Wunderlich et al. 1998; Bessette, Aslund et al. 1999; Bessette, Qiu et al. 2001). Active site mutant thioredoxins with glutaredoxin A active-site motif CPYC and eukaryotic PDI active site motif CGHC are preferred. Active site mutant DsbC isomerases with CGFC and CTFC active site motifs are preferred.

In U.S. Publication no. 20060246541, it was shown that VCN could be produced recombinantly in an active soluble form in Origami B (DE3) with an yield of 10-20 mg active product per liter of bacterial culture. However, this expression system will not produce soluble and/or active product in every case. The production of such disulfide-rich polypeptides in this system may be sequence dependent and a successful generation of a soluble and/or active product may only be achieved after significantly modifying (by sequence engineering) the original native sequences. To illustrate this point, when cloned into pET32a vector and expressed in Origami B (DE3), the native sequence of Echistatin does not yield a soluble product, its recombinant production being shifted into insoluble aggregates. Similarly, the native sequence of Controtrostatin cloned into pET32a vector is not expressed in the cytoplasm of Origami B as a soluble protein, with expression yields comparable to VCN, but it is an inactive product (a comparison between CN, VCN, and Echistatin sequences is shown in FIG. 1). Thus, the expression system described in U.S. Publication no. 20060246541 works for VCN but not for either parental native molecule. Furthermore, the generation of VCN in other bacterial hosts that also support disulfide bridge formation (e.g., the AD494 (DE3), a K12 derivative that carries the trxB mutation only, or the Rosetta-gami B (DE3), an Origami B derivative optimized for rare codon usage), does not appear to yield greater soluble VCN over that in Origami B (DE3).

Provided herein is a modified method of handling Origami B (DE3) cells transformed with VCN whereby a fast selection of transformants producing active VCN conformers is achieved. Specifically, the removal of the antibiotics that maintain the thioredoxin reductase and glutathione reductase mutations and thus the cytoplasmic microenvironment maximally oxidative has a beneficial effect on the selection of transformants optimized for the production of active VCN conformers.

When VCN is expressed in Origami B (DE3) in a fully selective medium (LB supplemented with Kanamycin and Tetracycline to maintain the thioredoxin reductase and glutathione reductase mutations, as well as Carbenicillin to select for pET32a transformants), and although VCN is generated as a soluble product with an expression yield of 10-20 mg/L as reported, the purified product does show a significant variability in activity from batch to batch. It is believed that the VCN product purified from a fusion generated by inducing expression in the presence of all three antibiotics is a mixture of active and inactive conformers and this composition varies from batch to batch.

A method that increases the amount of active versus inactive product is obtained by growing Origami B (DE3) cells transformed with VCN in the absence of the two antibiotics (Kanamycin and Tetracycline) that maintain the thioredoxin reductase and glutathione reductase mutations in this strain. The two redox mutations in Origami B are very stable and, therefore, this strain can be grown for multiple passages in the absence of the antibiotics and is still able to resume the normal growth when the antibiotics are added back to the growing media.

Origami B (DE3) VCN transformants grown in the absence of the two antibiotics that select for the thioredoxin reductase and glutathione reductase mutations grow faster, achieving higher densities compared to the cells grown in the presence of the two antibiotics. The increased growth rate appears to also be maintained during the induction period, the point after which recombinant production of a heterologous protein begins. Robust cell growth following induction of recombinant protein expression is important because this is when significant amounts of foreign protein begin accumulating in the bacterial cytoplasm, a process that usually has a negative impact on the growth of these transformants. However, in the embodiment of the invention when the selective pressure achieved using the two antibiotics that maintain thioredoxin reductase and glutathione reductase mutations is withdrawn, the consequence is that transformants with more desirable growth characteristics appear. Although not wishing to be bound by theory, this new transformant might display an optimized redox microenvironment to better counteract the stress caused by the accumulation of foreign proteins.

The removal of the antibiotics inducing expression of thioredoxin reductase and glutathione reductase negative mutants can occur before the induction phase of recombinant production and achieve increased expression levels. Antibiotic removal may also occur in conjunction with the induction phase or even soon after the induction phase. Increased expression is observed when cells are plated on Carbenicillin, Kanamycin and Tetracycline and further expanded with the three antibiotics but with induction of protein expression only in the presence of Carbenicillin (the antibiotic that is selective for the recombinant protein). Increased expression is observed when cells are plated and expanded in the presence of the three antibiotics with induction of protein expression only in the presence of Carbenicillin. In yet another approach, increased expression is observed when fresh transformants are plated, expanded and recombinant protein induced all in the presence of Carbenicillin but not Kanamycin and Tetracycline. In each case, there is a significant impact on cell growth (i.e., higher densities at the end of the induction period) and recombinant production (i.e., higher yields of soluble foreign proteins that translate into higher amounts of purified active conformers). The absence of Kanamycin and Tetracycline appears to be especially important during the induction period in this embodiment. This is particularly significant in the case of polypeptides like VCN which display no significant secondary structure and lots of cysteine residues that can pair to form a high number of disulfide bridge combinations, most of these combinations yielding a soluble but inactive product (i.e., of all possible conformers that can be combinatorially generated only those that fold an intact integrin binding loop yield active proteins). The methods of the invention are suitable for polypeptides having 2 or more disulfide bridges: the proteins expressed by the method can have at least 2, 3, 4, 5, 6, 7, 8, 9, or 10 disulfide bridges. The disulfide bridges can be intramolecular or intermolecular.

Figure 3:
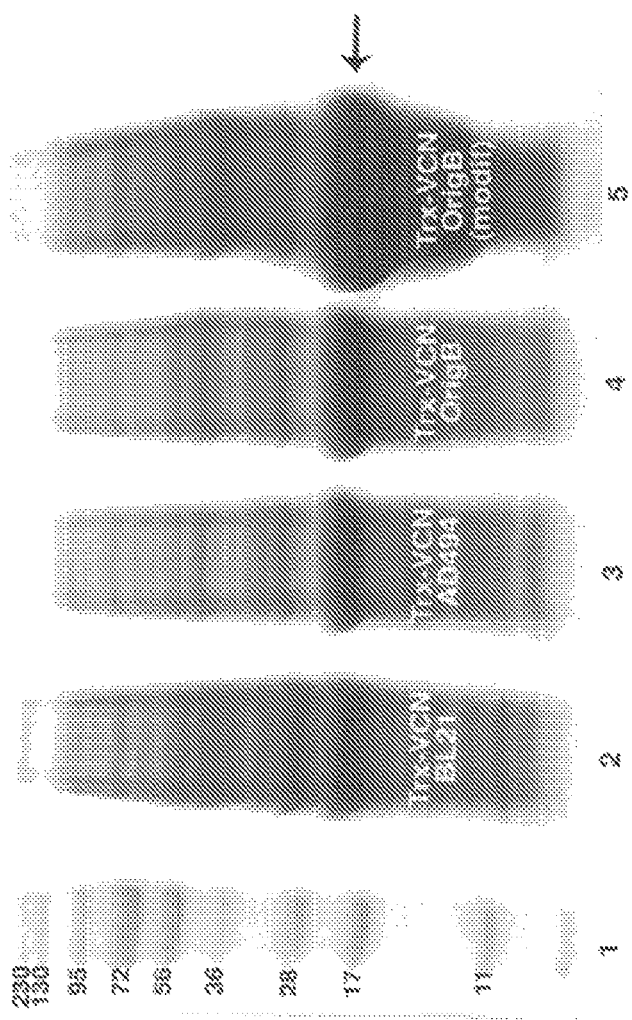
FIG. 3 depicts an SDS-PAGE Coomassie stained gel of soluble total protein fractions (TPF) collected from Origami B (DE3)pLysS *E. coli* host transformed with various Trx fusion constructs. Various *E. coli* cultures grown overnight at 37° C. in shake flasks were induced in 1 mM IPTG for 5 hours at 37° C. and 250 rpm. At the end of the induction period, the cells were pelleted at 4,000×g, lysed by sonication and further centrifuged at 40,000×g to remove the insoluble cell debris. 5 µl of soluble cell lysates from various *E. coli* hosts were loaded under reducing conditions on a precast 4-20% NuSep iGel (NuSep Inc., Lawrenceville, Ga.) and then Coomassie stained. From left to right, lanes represent: 1) PageRuler™ Plus Prestained Protein Ladder (Fermentas, Burlington, ON), 2) lysates from Trx-VCN-transformed BL21 (DE3) cells grown and induced in Carbenicillin, 3) lysates from AD494 (DE3) cells grown and induced in 2 AB (Carbenicillin and Kanamycin), 4) lysates from Origami B (DE3) cells grown and induced in 3 AB (Carbenicillin, Kanamycin and Tetracycline), and 5) lysates from Origami B (DE3) cells initially plated on 3 AB (Carbenicillin, Kanamycin and Tetracycline), but further expanded and induced in Carbenicillin only.

The following scenarios were observed when VCN was expressed in different bacterial hosts (FIG. 3). When VCN was expressed in an *E. coli* host that does not support formation of disulfide bridges (e.g., BL21 (DE3)), the recombinant product was not soluble and the production was shifted to insoluble aggregates. When VCN was generated in either AD494 (an *E. coli* strain that carries only the thioredoxin mutation) or in the double-mutant Origami B in the presence of all antibiotics required for the selection of the mutants, the heterologous protein was expressed as a soluble product, with an yield of approx. 10-20 mg/L, but as a mixture of active and inactive conformers. Lastly, the growing of Origami B VCN-transformants in the absence of the two selective antibiotics (Kanamycin and Tetracycline) appeared to be extremely beneficial in terms of both cell growth and active production yield, by significantly favoring the generation of active conformers and boosting the production yield to approx. 200 mg of purified product per liter of bacterial culture in shake flasks (FIG. 3).

The approach of removing the two antibiotics during growth of cells expressing VCN and obtaining a higher yield of active VCN was tried on both of the parent molecules, Contrortrostatin and Echistatin. In both cases, and unlike that of VCN expression, only inactive product was obtained.

The methods of increasing the yield of active VCN by inducing expressing in trxB/gor mutant host cells in the absence of antibiotics (Kan and Tet, respectively) that provide selective pressure to retain the mutant phenotype also can be applicable to other disulfide-rich proteins that normally express low amounts of active proteins in host cells cultured in the presence of these antibiotics.

The Origami B and other Origami strains which are based on FA113 and carry the trxB/gor mutant phenotype are available from Novagen, Madison Wis. It is believed that any of these strains may be used as host cells in the expression methods described herein.

The VCN produced in Origami B (DE3) using the instant method, wherein antibiotic selection is withdrawn to alter the redox environment of the bacterium, and otherwise processed as previously described (see FIG. 4 and Example 3) was analyzed head-to-head with native CN for binding activity as well as other functional assays. VCN was compared to CN for its signaling properties (e.g., the impact on global FAK phosphorylation) in suspended cells maintained in basal media and receiving no external inputs other than those coming from soluble disintegrins (see FIG. 5 and Example 5). VCN produced by the instant method was compared to native CN by flow cytometry for direct binding to multiple cell lines (see Example 6). VCN was also tested by flow cytometry for binding to cell surface receptors (MDA-MB-231 and MDA-MB-435 cell lines) in the presence of either competitors or EDTA (see Example 6). It also was shown that the cell surface-retained VCN (MDA-MB-435 cells) could be probed with polyclonal antisera raised against native CN and detected by flow cytometry. VCN and CN exhibited integrin binding activity (see Example 7). The anti-invasive (see FIGS. 6 and 7 and Examples 9 and 10) and anti-angiogenic (see FIG. 8-10 and Examples 11-13) effects of VCN were further tested in several in vitro assays and shown to be active.

Moreover, VCN generated by removing the antibiotics selecting for thioredoxin reductase and glutathione reductase mutations as disclosed herein was tested as a liposomal formulation in multiple in vivo human cancer xenograft models (e.g., the orthotopic MDA-MB-231 and MDA-MB-435 xenograft models etc) where it showed remarkable tumor growth inhibition and anti-angiogenic activity.

Methods of Use

Eukaryotic proteins produced as described herein may be used for treatment of various diseases and conditions for which the native protein may be used. Such proteins can be administered as a phainiaceutical or medicament formulated with a pharmaceutically acceptable carrier. Accordingly, the eukaryotic proteins may be used in the manufacture of a medicament or pharmaceutical composition.

Homodimeric and monomeric disintegrins described herein (e.g. VCN) may be used for any purposes for which native homodimeric disintegrins may be employed. Such uses are described in U.S. patent publication no. 2003/0186884, published Oct. 2, 2003.

In addition, homodimeric and monomeric disintegrins may be used to modulate the adhesion, motility, and invasiveness of integrin expressing tumor cells. When formulated as a pharmaceutically acceptable composition, such proteins can be used to treat patients by inhibiting or disrupting disease processes associated with a ligand binding to an $\alpha v\beta 3$ or $\alpha v\beta 5$ integrin.

Homodimeric and monomeric disintegrins described herein (e.g. VCN) may be used in methods to decrease the motility of an $\alpha v\beta 3$ integrin expressing cell, the method comprising cross-linking at least two $\alpha v\beta 3$ integrins on the integrin expressing cells thereby inhibiting the motility of said cells. Such crosslinking is believed to disrupt FAK signaling and activates tyrosine phosphorylation of FAK and CAS. Moreover, the crosslinking is believed to induce an alteration in cell morphology, including changes of cytoskeletal or focal adhesion structures. In a preferred embodiment, .alpha.v-.beta.3 integrin expressing cell is a tumor cell.

Homodimeric and monomeric disintegrins described herein (e.g. VCN) may be used to inhibit the adhesion of integrin expressing cells to vitronectin by exposing the cells to the homodimeric and monomeric disintegrin. The homodimeric and monomeric disintegrin is believed to inhibit adhesion by binding to an integrin, in particular $\alpha v\beta 3$ or $\alpha v\beta 5$ integrin.

Homodimeric and monomeric disintegrins described herein (e.g. VCN) may be formulated as compositions for the treatment of thrombotic diseases in mammals, alone or in conjunction with one or more thrombolytic agents. In particular, such compositions have utility in treating or preventing arterial, venous and microvascular thrombosis and thromboembolism. Such compositions also have utility in treating stroke, transient ischemic attacks, arteriosclerosis, atherosclerosis, pulmonary embolism, aneurisms and angina. In particular, such compositions have utility in preventing or treating myocardial infarctions.

Homodimeric and monomeric disintegrins described herein (e.g. VCN) may be used to inhibit metastasis in melanoma, carcinoma and sarcoma patients. In particular embodiments Homodimeric and monomeric disintegrins may be used to prevent metastasis in breast cancer patients.

Homodimeric and monomeric disintegrins described herein (e.g. VCN) may be used to treat osteoporosis. Compositions and methods for treatment of osteoporosis employing an amount of a homodimeric and monomeric disintegrin effective to inhibit bone resorption by osteoclasts may be used.

Homodimeric and monomeric disintegrins described herein (e.g. VCN) may be used to promote wound healing. Homodimeric and monomeric disintegrins may inhibit cell-cell and cell-extracellular matrix interactions (including interaction with fibronectin), thus promoting wound repair, including keloid formation. Compositions containing homodimeric and monomeric disintegrins may be used to prevent adhesion formation when administered to a patient in need of such treatment.

Pharmaceutical compositions containing homodimeric and monomeric disintegrins should comprise at a minimum an amount of protein effective to achieve the desired effect (i.e., prevent thrombus formation, prevent metastasis in carcinoma patients, prevent adhesion formation, etc.) and a suitable carrier or excipient. Generally, in these compositions, homodimeric and monomeric disintegrins are present in an amount sufficient to provide about 0.01 mg/kg to about 50 mg/kg per day, preferably about 0.1 mg/kg to about 5.0 mg/kg per day, and most preferably about 0.1 mg/kg to about 0.5 mg/kg per day. Such compositions have particular utility in the prevention of thrombus formation.

Homodimeric and monomeric disintegrins may be administered in combination with at least one thrombolytic agent present in an amount effective to achieve thrombolysis. Suitable thrombolytic agents include, but are not limited to, the following: anisoylated plasminogen streptokinase activator complex (APSAC); tissue-type plasminogen activator (tPA); urokinase-type plasminogen activator (uPA); and fibrolase, a snake venom fibrinolytic agent as described in U.S. Pat. No. 4,610,879 to Markland, Jr. et al.

Homodimeric and monomeric disintegrins may be administered by a variety of heretofore known means suitable for delivery thereof into the blood stream in substantial amounts. Intravenous administration of homodimeric and monomeric disintegrins in a suitable liquid vehicle or excipient is presently contemplated as the preferred route of administration. Homodimeric and monomeric disintegrins are soluble in water, and may therefore be effectively administered in a suitable aqueous solution (e.g., phosphate buffered saline). Alternatively, Homodimeric and monomeric disintegrins may be administered orally (in the form of tablets or capsules formulated with a suitable binder or excipient material, or in the form of aqueous or oily suspensions, solutions, emulsions, syrups or elixirs) or as a parenteral suspension. As is well known in the art, adjuvants such as local anesthetics, preservatives, buffering agents, lubricants, wetting agents, colorants, flavorings, fillers and diluents may suitably be included in any of these formulations.

The versatility of the invention is illustrated by the following Examples which illustrate preferred embodiments of the invention and are not limiting of the claims or specification in any way.

EXAMPLES

Example 1

Controtrostatin Purification

Venom of Agkistrodon contortrix contortrix was purchased from Miami Serpentarium (Punta Gorda, Fla.). CN was purified in a four-step high-performance liquid chromatography (HPLC) procedure according to an established protocol (Trikha, M. et al., 1994).

Example 2

Cells and Reagents

The MDA-MB-435 cells (American Type Culture Collection, Manassas, Va.) were obtained from Dr. Janet Price (MD Anderson Cancer Center, Houston, Tex.) and the MDA-MB-231 cells (American Type Culture Collection, Manassas, Va.) from Dr. Toshiyuki Yoneda (Osaka University, Osaka, Japan). HUVEC were purchased from PromoCell (Heidelberg, Germany) and maintained according to the manufacturer's protocol. The Origami B (DE3) E. coli strain and pET32a expression vector carrying the bacterial thioredoxin A gene (trxA) were purchased from Novagen (San Diego, Calif.). The oligonucleotide primers used for VCN cloning were synthesized by Operon Biotechnologies, Inc. (Huntsville, Ala.). A southern copperhead venom gland cDNA library, a mouse CN monoclonal antibody, and rabbit CN polyclonal antiserum (Alpha Diagnostic International, San Antonio, Tex.) are available in the Markland laboratory at the University of Southern California. The 'Endothelial Cell Tube Formation' plates were purchased from BD Biosciences (San Jose, Calif.). The tube formation inhibitor Suramin, the actin modifier Cytochalasin D, and the cyclo(Arg-Gly-Asp-DPhe-Val) peptide were purchased from Calbiochem (San Diego, Calif.). The fluorometric cell invasion assay kit (QCM™ 24-Well Cell Invasion) was from Millipore (Billerica, Mass.). The complete Matrigel was from BD Biosciences (Bedford, Mass.). The recombinant TEV protease, Calcein AM, and Rhodamine-Phalloidin were purchased from Invitrogen (Carlsbad, Calif.). A column-based FITC-labeling kit (EZ-Label) and an endotoxin removal kit were purchased from Pierce (Rockford, Ill.). The DeadEnd™ Fluorometric TUNEL assay kit was from Promega (Madison, Wis.). The non-selective protein kinase inhibitor Staurosporine was from Cayman Chemical (Ann Arbor, Mich.). The mouse 03 integrin 7E3 F(ab')2 antibody fragment was a gift from Dr. Marian Nakata (Centocor, Horsham, Pa.). The mouse $\alpha v\beta 3$ integrin antibody LM609 was from Millipore. The CD31 polyclonal antibody (MEC13.3) was from BD Pharmingen (Franklin Lakes, N.J.). The Ki-67 (H-300), a FAK polyclonal (A-17), and all secondary antibodies were purchased from Santa Cruz Biotechnology (Santa Cruz, Calif.). A FAK monoclonal antibody (clone 77) was from BD Biosciences (Bedford, Mass.). A phosphotyrosine monoclonal antibody (P-Tyr-102) was from Cell Signaling Technology (Danvers, Mass.). Purified soluble $\alpha v\beta 3$ and $\alpha v\beta 5$ integrins were purchased from Millipore and soluble recombinant $\alpha 5\beta 1$ integrin from R&D Systems (Minneapolis, Minn.). All other reagents were purchased from Sigma Chemical Co. (St. Louis, Mo.). Avastin (Genentech, South San Francisco, Calif.) was a gift from Dr. Augustin Garcia (Norris Comprehensive Cancer Center, University of Southern California).

Example 3

Construction of VCN Expression Vectors and Recombinant Production

VCN was cloned into pET32a vector downstream of TrxA using a BglII/NcoI set of restriction enzymes. The forward primer for VCN introduced a unique TEV protease cleavage site, which made possible the removal of thioredoxin during purification. To build the VCN construct, the nucleotides encoding the C-terminal tail of echistatin were added to CN via an elongated reverse primer. The primers used for VCN were: forward-5' gttccagatctcgagaatctttacttc-caaggagacgctcctgcaaatccgtgctgcga3', and reverse-5' gttat-tcgccatggettaagtagctggac-ccagtggggatttctgggacagccagcagatatgcc3'. The plasmid was initially amplified in DH5α E. coli, purified and sequenced, and then transferred into various E. coli hosts. Multiple cultures were established for each construct from individual colonies of transformed BL21 (DE3), AD494 (DE3) or Origami B (DE3) in LB media containing either carbenicillin (50 μg/mL) alone, or carbenicillin (50 μg/mL) plus kanamycin (15 μg/mL) or carbenicillin (50 μg/mL) plus tetracycline (12.5 μg/mL), plus kanamycin (15 μg/mL) and grown at 37° C. and 250 rpm in a shaker-incubator until they reached an $OD_{600}$ of 0.6-1. At this point, the cells from all cultures were induced in 1 mM IPTG and incubated for another 4-5 hours at 37° C. and 250 rpm. At the end of the induction period, the cells were pelleted at 4000×g and lysed in a microfluidizer (Microfluidics M-110L, Microfluidics, Newton, Mass.). The operating conditions of the microfluidizer included applied pressures of 14,000-18,000 psi, bacterial slurry flow rates of 300-400 ml per minute and multiple passes of the slurry through the processor. The lysate insoluble cellular debris was removed by centrifugation (40,000×g) and the soluble material containing Trx-VCN collected. The expressed fusion protein in the collected soluble lysates was then proteolysed by incubation with recombinant TEV protease overnight at room temperature which efficiently cleaved off VCN from TrxA as monitored by SDS-PAGE. When proteolysis was complete, the proteolyzed lysates were passed through a 0.24 μm filter, diluted 1:100 in ddH$_2$O, ultrafiltrated through a 50,000 MWCO cartridge (Biomax50, Millipore) and then reconcentrated against a 5,000 MWCO cartridge (Biomax5, Millipore) using a tangential flow ultrafiltration device (Labscale TFF system, Millipore).

FIG. 3 shows an SDS-PAGE Coomassie stained gel of soluble total protein fractions (TPF) collected from Origami B (DE3)pLysS E. coli host transformed with various Trx fusion constructs. Lysates from Origami B (DE3) cells initially plated on 3 AB (Carbenicillin, Kanamycin and Tetracycline), but further expanded and induced in Carbenicillin only demonstrated a much greater induction of VCN product.

Figure 4:
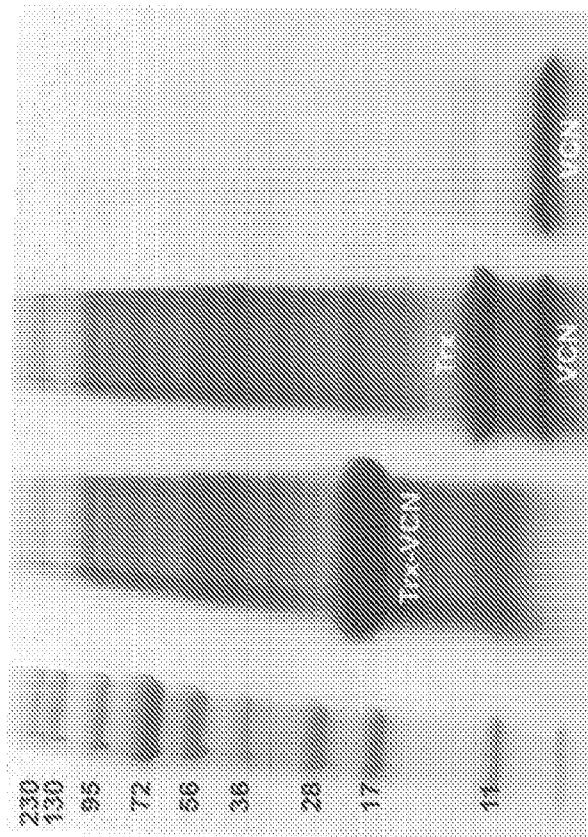
FIG. 4 depicts an SDS-PAGE Coomassie stained gel of soluble total protein fractions (TPF) collected from Origami B (DE3)pLysS *E. coli* host transformed with Trx-VCN fusion constructs. A 10 L transformed Origami B (DE3) *E. coli* culture grown overnight at 37° C. in shake flasks in the presence of Carbenicillin was induced in 1 mM IPTG for 5 hours at 37° C. and 250 rpm. At the end of the induction period, the cells were pelleted at 4,000×g, the bacterial paste diluted 20× in water, homogenized in a microfluidizer and further centrifuged at 40,000×g to remove the insoluble cell debris. 5 µl of the generated soluble cell lysates (in the presence or absence of TEV) or HPLC-purified VCN were loaded under reducing conditions on a precast 4-20% NuSep iGel (NuSep Inc., Lawrenceville, Ga.) and then Coomassie stained. From left to right, lanes represent: PageRuler™ Plus Prestained Protein Ladder (Fermentas, Burlington, ON), lysates from Trx-VCN-transformed cells, TEV-treated lysates, and HPLC-purified VCN. During this procedure, approx. 200 mg of HPLC-purified VCN was generated from 1 L of bacterial culture.

FIG. 4 shows an SDS-PAGE Coomassie stained gel of soluble total protein fractions (TPF) collected from Origami B (DE3)pLysS E. coli host transformed with Trx-VCN fusion constructs. The VCN product of a TrxA-VCN fusion was efficiently cleaved from TrxA by proteolysis using TEV. Unlike the BL21 (DE3) strain, the lysates from both AD494 (DE3) and Origami B (DE3) strains generate a unique and consistent Trx-VCN band (shown by the arrow). The instant methods of the invention achieved higher cell densities at the end of the induction time, generating up to 200 mg of soluble VCN per liter of bacterial culture after purification.

Example 4

Purification of Recombinant Disintegrins

Purification of recombinant disintegrins was performed by C18-reverse phase HPLC using the standard elution conditions previously employed for the purification of native CN (Trikha, M. et al., 1994). The filtrated lysates processed as described above were loaded onto a Vydac C18 column (218TP54, Temecula, Calif.). A ten-minute rinse (at 5 ml/min) of the column with an aqueous solution containing 0.1% TFA was followed by a linear gradient (0-100%) elution over 150 min in a mobile phase containing 80% acetonitrile and 0.1% TFA. Recombinant VCN starts eluting in 35% acetonitrile.

Example 5

FAK Phosphorylation Studies

Serum-starved MDA-MB-435 cells were harvested by limited trypsin/EDTA treatment (Ritter, M. et al., 2000) and maintained in suspension before being exposed for 10-30 min to different concentrations of either native CN or VCN. The cells were lysed and the soluble fraction immunoprecipitated with a polyclonal FAK antibody (clone A-17) and further assayed by Western blotting (Ritter, M. et al., 2000; Schmitmeier, S. et al., 2005). The transferred proteins were probed with either a p-Tyr antibody (P-Tyr-102, Cell Signaling Technology, Danvers, Mass.) or a monoclonal FAK antibody (clone 77, BD Biosciences, Bedford, Mass.).

Figure 5:
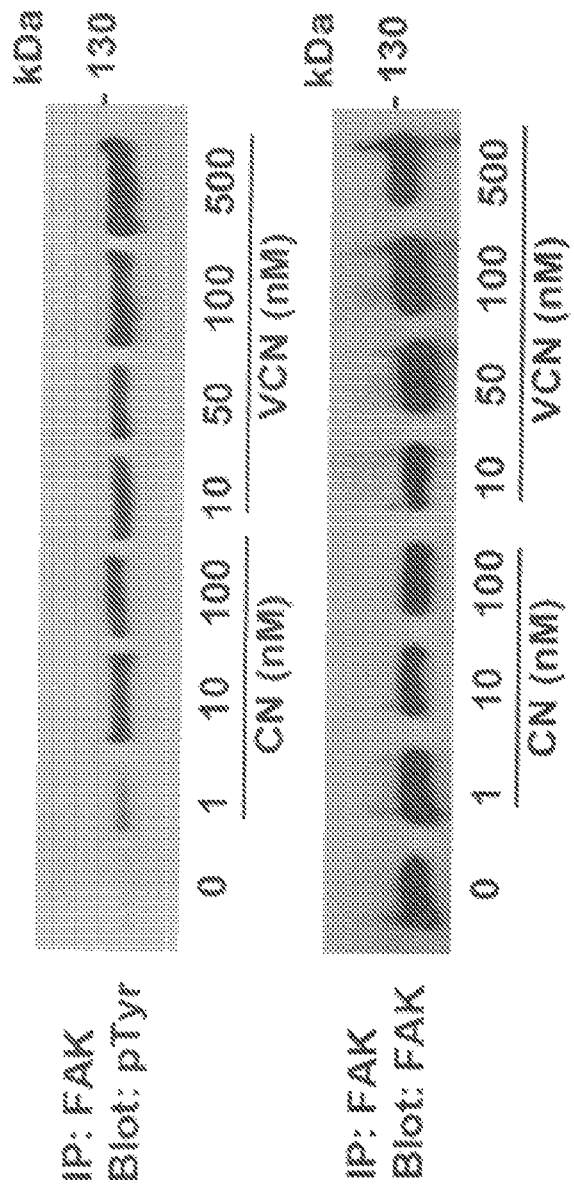
FIG. 5 shows FAK phosphorylation levels in MDA-MB-435 cells treated with soluble disintegrins by Western blotting. The cells were kept in suspension in serum-free media and incubated with various amounts of either CN or VCN for 10-30 min. The agonistic activity of both CN and VCN was assessed based on their effect on the global level of FAK phosphorylation by Western blotting.

FIG. 5 shows that CN and VCN show comparable effect on global FAK phosphorylation.

Example 6

Cell Surface Binding Studies by Flow Cytometry

HUVEC, MDA-MB-231 or MDA-MB-435 cells were grown to early confluency and starved overnight in serum-free media. The cells were harvested and resuspended in 1 ml of serum-free media ($5 \times 10^5$ cells/condition) before being incubated with different treatments or controls for 30 min at 37° C. At the end of the incubation period, the cells were pelleted, washed in ice-cold PBS containing 5% fetal bovine serum and either analyzed in a FACSCalibur scanner (BD Biosciences, Bedford, Mass.) or, depending on the assay, further incubated at 4° C. for 30 minute intervals with additional treatments. All cells were counterstained with propidium iodide to allow gating of necrotic cells. For each reading, 10,000 cells per sample were analyzed.

MDA-MB-435 cells were preincubated with either VCN or CN and then probed with either polyclonal antisera raised against native CN. The bound primary antibody was then detected with an anti-rabbit FITC-labeled secondary antibody. The controls included cells incubated with either anti-rabbit FITC-labeled secondary only or anti-CN primary followed by the FITC-labeled secondary in the absence of disintegrins. In another series of experiments, MDA-MB-435 cells were either directly probed with FITC-CN or preincubated with FITC-CN, washed and then resuspended in 3 mM EDTA or preincubated in 3 mM EDTA, then washed and probed with FITC-CN or probed with an irrelevant FITC-labeled antibody. In another series of experiments, MDA-MB-435 cells were either directly probed with FITC-VCN or preincubated with FITC-VCN, washed and then resuspended in 3 mM EDTA or preincubated in 3 mM EDTA, then washed and probed with FITC-VCN or probed with an irrelevant FITC-labeled antibody. Flow cytometric analysis showed that both native CN and recombinant VCN can be detected at the cell surface when probed with polyclonal antisera. Furthermore, EDTA preincubation prevents the binding of both labeled disintegrins, whereas the eventual addition of EDTA does not displace the already bound labeled disintegrins.

In other experiments, MDA-MB-435 cells, MDA-MB-231 cells or HUVEC were either incubated with FITC-CN or FITC-VCN or probed with an irrelevant FITC-labeled antibody. Flow cytometric analysis showed that the labeled recombinant VCN and native CN bind in a similar manner to both cancer cells lines MDA-MB-435 cells and MDA-MB-231 cells and HUVEC.

In other experiments, MDA-MB-435 or MDA-MB-231 cells were either preincubated with unlabeled VCN and then probed with FITC-CN or preincubated with unlabeled 7E3 monoclonal antibody and then probed with FITC-CN or directly probed with FITC-CN only or with an irrelevant FITC-labeled antibody. In other experiments, MDA-MB-435 or MDA-MB-231 cells were either preincubated with unlabeled CN and then probed with FITC-VCN or preincubated with unlabeled 7E3 monoclonal antibody and then probed with FITC-VCN or directly probed with FITC-VCN only or with an irrelevant FITC-labeled antibody. Flow cytometric analysis showed that the pretreatment with unlabeled disintegrins or 7E3 monoclonal antibody, a direct competitor for the RGD tripeptide motif, prevented the further binding of either labeled disintegrin.

Example 7

Integrin Binding Kinetics by Fluorescence Polarization (FP)

Differing concentrations of purified soluble functional integrins (i.e., $\alpha v \beta 3$, $\alpha v \beta 5$ or $\alpha 5 \beta 1$) were incubated with a constant amount of FITC-labeled VCN or CN using an established protocol (Park, S. et al., 2004). Upon binding to the much larger integrin, the fluorescent tag on either disintegrin tumbles in solution at a slower rate compared to the unbound state resulting in increased levels of polarization. The measured FP value is a weighted average of FP values of the bound and free fluorescent disintegrins and is therefore a direct measure of the bound fraction. The data were analyzed as for standard radioligand binding, and kinetics of binding determined using Scatchard analysis and a non-linear curve fit. The data were generated in a PTI QuantaMaster QM-4SE spectrofluorometer (Photon Technology International, Birmingham, N.J.) using the PTI FeliX32 software for data acquisition and Prism v3.02 (GraphPad Software, La Jolla, Calif.) for data analysis.

Results of integrin binding kinetic analysis shown in Table 1 below demonstrate CN and VCN actively bind to the integrins $\alpha v \beta 3$, $\alpha v \beta 5$ or $\alpha 5 \beta 1$.

TABLE 1

| Disintegrin | Integrin Kd (+/−SD) | | |
| --- | --- | --- | --- |
| | $\alpha v \beta 3$ | $\alpha 5 \beta 1$ | $\alpha v \beta 5$ |
| CN | 6.6 nM (0.8) | 191.3 nM (65.2) | 19.5 nM (5.7) |
| VCN | 7.4 nM (0.4) | 15.2 nM (4.2) | 41.2 nM (12.3) |

Example 8

Cell Viability and Proliferation Studies

HUVEC, MDA-MB-231 or MDA-MB-435 cells were plated in complete media on either plastic or Matrigel-coated 24-well plates ($5 \times 10^4$ cells/well) and allowed to adhere. Native CN or VCN were added to the wells at concentrations ranging from 1-1000 nM. Cells receiving no treatment or Actinomycin D were used as controls. The number of viable cells for each condition was quantified colorimetrically after 24 hr of incubation using the Cell Titer 96 AQueous cell viability kit (Promega, Madison, Wis.) according to the manufacturer's protocol. The cell viability was further confirmed by TUNEL staining. To assess the impact of native CN or VCN on cell proliferation, early passages of HUVEC, MDA-MB-231 or MDA-MB-435 were seeded in Matrigel-coated T25 flasks ($2\times10^5$ cells/flask) in complete media in the presence of various concentrations of disintegrins. The cells were allowed to grow for 3 days, harvested, counted, and the numbers averaged and plotted.

Example 9

Inhibition of Cell Migration (the Colloidal Gold Migration Assay)

The ability of disintegrins to interfere with HUVEC, MDA-MB-231 or MDA-MB-435 cell migration was assessed on glass coverslips homogenously covered with a fine layer of colloidal gold salt. The assay represents a modified form of an assay of cellular migration first described in 1977 (Albrecht-Buehler, G., 1977) and was used initially to investigate the pattern and direction of migrating fibroblasts but thereafter adapted for the quantitative analysis of cell motility using other cell types, including endothelial cells (Zetter, B., 1980; Bowersox, J. et al., 1982). This assay is based on the phenomenon that migrating cells are able to push to one side, collect (on their dorsal surface) and/or phagocytose small particles in their path on the substratum on which they move (Abercrombie, M. et al., 1970; Albrecht-Buehler, G., 1977). This activity generates particle-free tracks ('phagokinetic tracks') on a densely particle-coated migratory substrate that can act as a permanent record of cellular movement. The gold chloride solution was prepared using Hydrogen Tetrachloroaurate(III) (also known as Tetrachloroauric (III) acid, molecular formula $HAuCl_4.3H_2O$, Sigma-Aldrich) 0.342 g dissolved in 50 ml purified distilled $H_2O$. This was vigorously vortexed until fully dissolved. Clean round glass coverslips 2.2 cm diameter (VWR International) were gasped with forceps at one edge and dipped into the solution of 1% BSA. With great care the glass slips were repeatedly dipped into the solution and withdrawn, over a period of several minutes. The BSA slowly adhered to the glass and this process provided for a better and more uniform coating. Excess BSA was allowed to drain off the coverslips at an angle after which the slips were dipped once in 100% ethanol. The slips thus prepared were then dried gently but rapidly with a hand held hair dryer at medium settings (temperature approximately 85° C. at 10-15 cm from the dryer). Once coated and dried each glass slip was placed into one well of a 12 well cell culture plate (VWR International). The BSA coated coverslips in the 12 well cell culture plates were then coated with gold salt. Small particles of a mixture of gold salts were deposited onto the BSA on each glass slip as a solution of colloidal gold salt freshly prepared was placed on the slips and allowed to cool. The colloidal gold salt solution was prepared by mixing reagents as described below and 1 ml of the solution was sufficient to coat each glass slip in each well. In an 125 ml Erlenmeyer flask the following reagents were mixed at room temperature: 20.8 ml of purified distilled $H_2O$, 12.0 ml of the sodium carbonate ($Na_2CO_3$) solution, and 3.6 ml of Gold Chloride ($HAuCl_4. 3H_2O$) solution, also as prepared above. Over a naked Bunsen burner flame the mixture was gradually heated while continually, but very gently swirling the liquid. Immediately, as the solution reached the boiling point it was removed from the heat and 3.6 ml of the 0.1% w/v formaldehyde was added (an equal volume to that of the Gold Chloride solution) while continuing very gentle swirling. The successful preparation of a colloidal gold salt solution was indicated by the solution turning brownish in color. This mixture was then immediately pipetted into the wells of the 12 well cell culture plates containing the BSA coated glass slips, 1 ml per well. The plates were allowed to incubate undisturbed (and covered) during which time gold particles were deposited onto the BSA coated glass slips in a sterile manner. After incubation the residual liquid (remaining colloidal gold salt solution) was aspirated from each well. Each well was then rinsed with Hank's Buffered Salt Solution with calcium chloride and magnesium sulphate (HBSS+) (Sigma-Aldrich). 1 ml of HBSS+ was added to each well and the plate was gently rocked for 10-15 s. The HBSS+ was then aspirated and a further 1 ml of HBSS+ was added. Microscopic visual inspection of the wells was then performed under 100-200× magnification (Olympus CK2 inverted phase contrast microscope, or Zeiss Axioplan-2 optical microscope). The prepared gold coverslips were further covered with a layer of tumorigenic ECM matrix (complete Matrigel) which was done overnight at 37° C. Early passages of serum-starved HUVEC, MDA-MB-231 or MDA-MB-435 cells were then seeded on these coverslips (approximately 3000 cells/well) in the presence of various treatments and allowed to migrate at 37° C. in the presence of 5% $CO_2$ for up to 48 hrs depending on the cell line after which the cells were fixed in 4% formaldehyde and further imaged. The quantification of the cellular migration was done by computer-assisted image analysis in which each pixel corresponding to the 'phagokinetic tracks' were counted digitally with the 'SimplePCI' imaging software (C-Imaging Systems, Cranberry Township, Pa.). The total number of pixels in the 'phagokinetic track' areas left by motile cells were averaged (by analysing 25 randomly selected microscopic fields per treatment condition captured at 200× magnification) and compared to controls.

Figure 6:
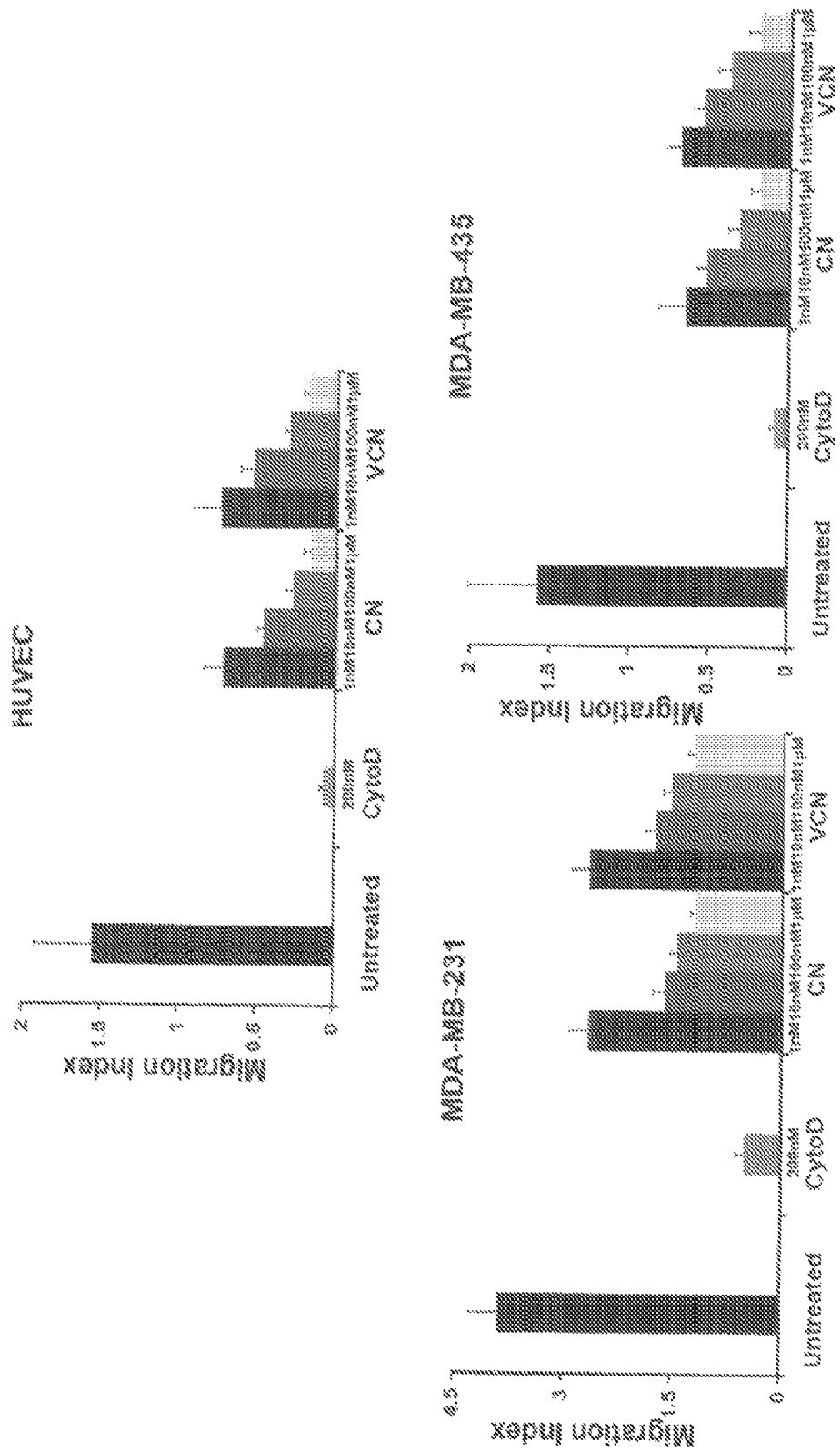
FIG. 6 shows inhibition of cell migration on a tumorigenic ECM by disintegrins using a colloidal gold migration assay. The ability of VCN to interfere with cell migration was assessed on serum-starved HUVEC, MDA-MB-231 or MDA-MB-435 cells seeded on top of Matrigel-coated (BD Biosciences) coverslips that had been uniformly covered with a fine layer of colloidal gold salt. The fungal metabolite Cytochalasin D, a potent inhibitor of actin polymerization, was used as a positive control at a concentration of 200 nM. For quantitation of cell migration, 25 randomly selected microscopic fields were analyzed ('SimplePCI') per treatment and plotted against the controls.

FIG. 6 shows that random cell migration pushes the gold particles away thus creating denuded gold-free areas ('tracks') that were quantitated by computer-assisted analysis. For quantitation of cell migration, 25 randomly selected microscopic fields were analyzed ('SimplePCI') per treatment and plotted against the controls. The data were averaged from at least three independent experiments for each cell line tested. The results show that CN and VCN display comparable inhibition of migration in all three cell types tested.

Example 10

Inhibition of Cell Invasion Using a Transwell Invasion Assay

The ability of disintegrins to block the invasion of HUVEC, MDA-MB-231 and MDA-MB-435 cells through a reconstituted basement membrane was assessed using the fluorometric QCM™ 24-Well Cell Invasion kit (Millipore, Billerica, Mass.). The cells were serum-starved overnight, harvested, resuspended in serum-free media ($1\times10^6$ cell/ml) and incubated in the presence of various concentrations (0-1000 nM) of either native CN or VCN for 10 min at 37° C. The assay was done according to the manufacturer's protocol and used HT1080 conditioned media as a chemoattractant. The invasion plates were incubated for up to 48 hr (depending on the cell line) at 37° C. in the presence of 5% $CO_2$. At the end of the incubation period, the invaded cells were detached, lysed and quantitated using the DNA-binding fluorescent dye CyQUANT. The relative fluorescence was measured in a SPECTRAmax GeminiEM fluorescent plate reader (Molecular Devices, Sunnyvale, Calif.) and the numbers averaged and plotted for each condition.

Figure 7:
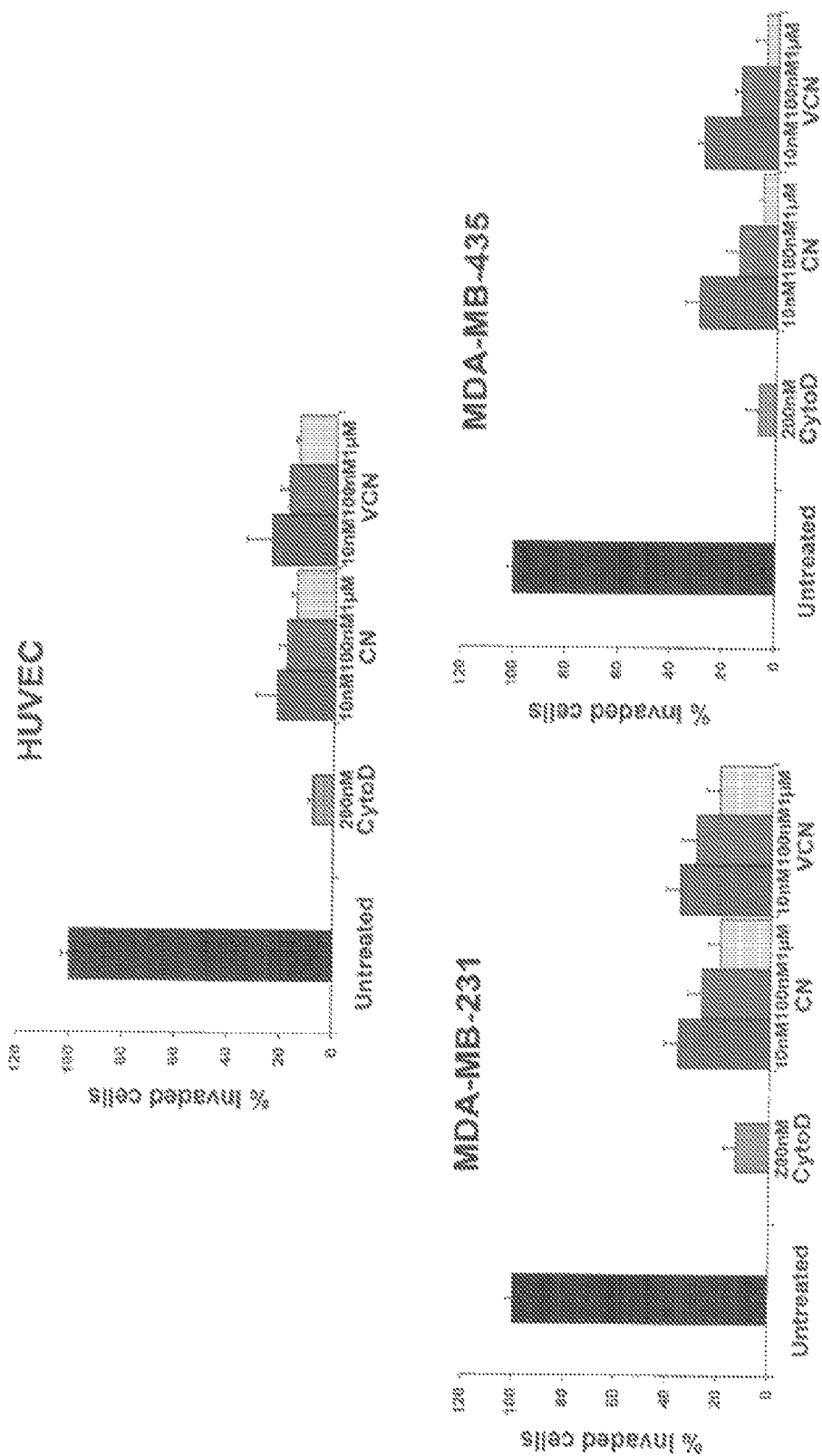
FIG. 7 shows inhibition of cell invasion through a reconstituted basement membrane using a transwell invasion assay. The anti-invasive properties of VCN were tested in a modified Boyden chamber assay where serum-starved HUVEC, MDA-MB-231 or MDA-MB-435 cells were preincubated with various concentrations of disintegrins (10-1000 nM) for 10 min before being seeded into Matrigel-coated (ECMatrix™, Millipore) porous inserts (pore size, 8 µm) and allowed to invade against a chemoattractant gradient (HT1080 human fibrosarcoma conditioned media) for up to 48 hr. At the end of the incubation time, the cells that invaded into the lower chamber were detached, lysed, stained with CyQuant and quantitated in a fluorescent plate reader. The fungal metabolite Cytochalasin D, a potent inhibitor of actin polymerization, was used as a positive control at a concentration of 200 nM.

FIG. 7 shows the results of the transwell invasion assay. The data were averaged from at least three independent experiments for each cell line tested. The results show that CN and VCN display comparable inhibition of migration in all three cell types tested.

Example 11

Inhibition of HUVEC Tube Formation

'Endothelial Tube Formation' plates precoated with Matrigel (BD Biosciences, Bedford, Mass.) were used according to the manufacturer's protocol. HUVEC were seeded in triplicate ($3 \times 10^4$ cells/well) in the presence of various concentrations (0-1000 nM) of either native CN or VCN and incubated for 16 hr at 37° C. in the presence of 5% $CO_2$. The tube formation inhibitor Suramin was used as a positive control. At the end of incubation period, cells were stained with Calcein AM and imaged by confocal microscopy (LSM 510 Confocal/Titanium Sapphire Laser). The total length of tubes for each condition was quantitated in multiple fields using the Zeiss LSM Image Browser (Carl Zeiss MicroImaging GmbH, Munich, Germany) and averaged from at least three independent experiments.

Figure 8:
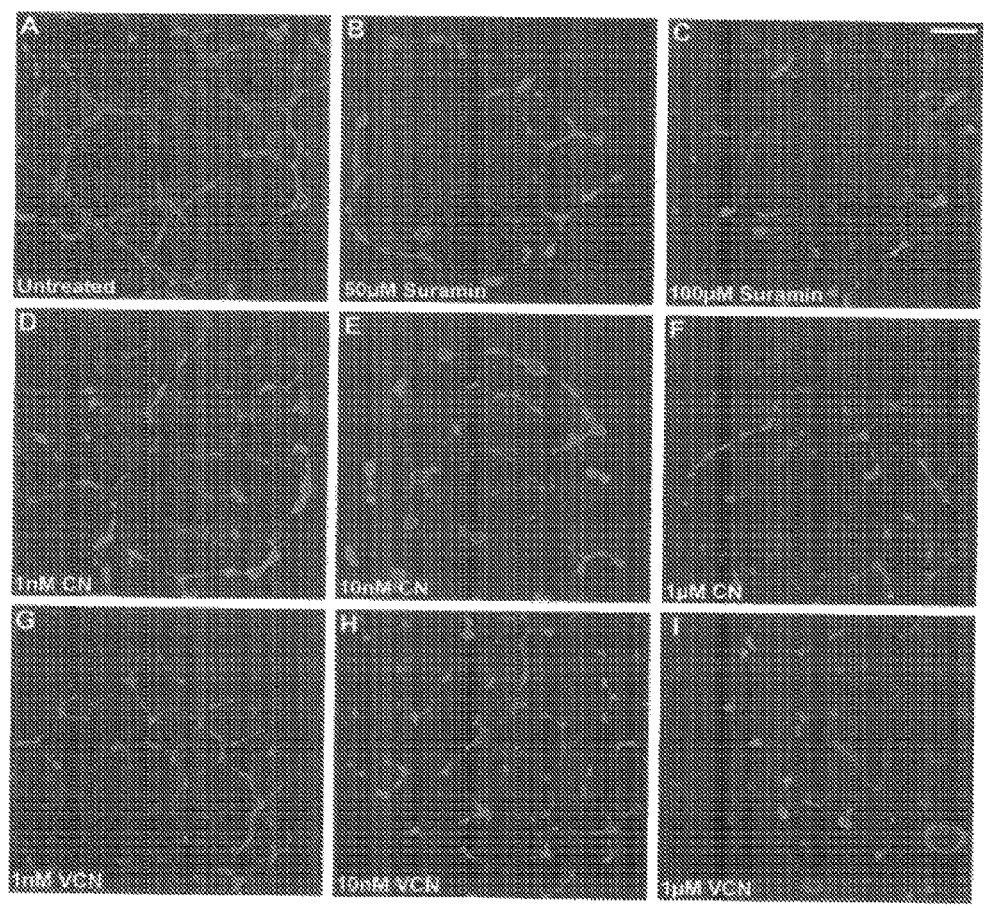
FIG. 8 shows inhibition of HUVEC tube formation by disintegrins by confocal microscopy. HUVEC cells were plated on 'Endothelial Cell Tube Formation' plates (BD Biosciences) in the presence of various concentrations of either CN or VCN (1-1000 nM). A known tube formation inhibitor (Suramin) was used as a negative control. Representative figures from three independent experiments are shown above: panel A—untreated control; panel B—50 µM Suramin; panel C—100 µM Suramin; panel D—1 nM CN; panel E—10 nM CN; panel F—1000 nM CN; panel G—1 nM VCN; panel H—10 nM VCN; panel I—1000 nM VCN. Cells were stained with Calcein AM and imaged using confocal microscopy. All images were taken at the same magnification (scale bar=50 µm).
Figure 9:
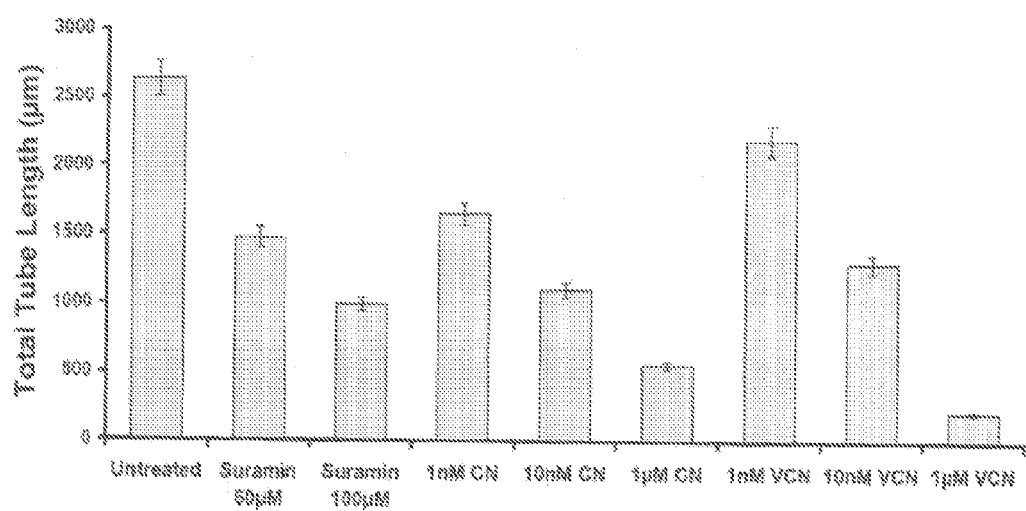
FIG. 9 shows tube formation inhibition by various amounts of CN or VCN by confocal microscopy. The tubes formed by HUVECs were quantitated in multiple fields collected from three repeated experiments by computing the total tube length with Zeiss LSM image software and averaged to form each data point.

FIG. 8 shows confocal image results and FIG. 9 length measurement results of the endothelial tube formation assay. CN and VN showed comparable effect on reducing tube formation compared to control.

Example 12

Disruption of Actin Cytoskeleton Organization

HUVEC grown in complete media were seeded in triplicate in 8-well chamber slides coated with complete Matrigel (4×104 cells/well). Each well received different concentrations of various treatments {including FITC-CN, FITC-VCN, the cyclic RGD peptide cyclo(Arg-Gly-Asp-DPhe-Val) (abbreviated cRGDfV), or the 7E3 F(ab')2 antibody fragment}. The actin modifier Cytochalasin D (CytoD) was used as a positive control. The cells were incubated with the treatments for 3 hr at 37° C. in the presence of 5% CO2. At the end of the incubation period, the cells were washed, incubated with secondary treatments (depending on the condition), fixed in 4% formaldehyde, permeabilized in 0.1% Triton X-100 in PBS, and then stained with Rhodamine-Phalloidin and counter-stained with Hoechst 33342 before being imaged by confocal microscopy (LSM 510 Confocal/Titanium Sapphire Laser).

Example 13

In Vitro HUVEC Apoptosis Studies

HUVEC seeded in serum-free media in 8-well chamber slides coated with complete Matrigel (4×104 cells/well) were allowed to adhere before being sandwiched with another layer of Matrigel that was uniformly pipetted on top of the adherent cells. The second Matrigel layer was allowed to settle before various treatments were added and chambers incubated at 37° C. in the presence of 5% $CO_2$ for approximately 16 hr. At the end of the incubation period, the cells were fixed in 4% formaldehyde, permeabilized in 0.2% Triton X-100 in PBS, TUNEL stained using the DeadEnd™ Fluorometric kit (Promega, Madison, Wis.), and counter-stained with Rhodamine-Phalloidin and Hoechst 33342. The % cell death was quantitated in random fields taken at ×250 magnification using the formula 'number of TUNEL+ nuclei/total number of nuclei ×100' for each treatment group.

Figure 10:
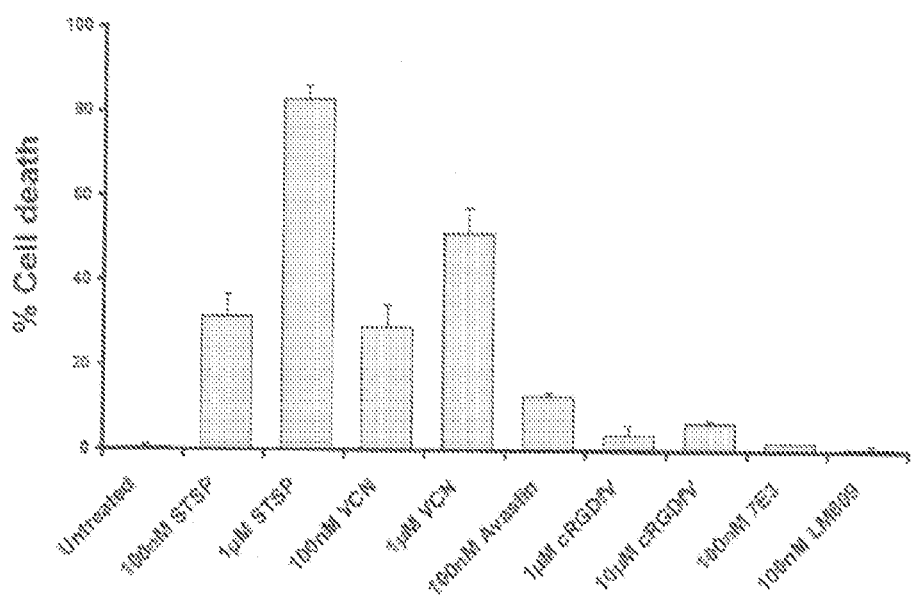
FIG. 10 shows that VCN induces apoptosis in tubulogenic HUVEC seeded between two Matrigel layers. HUVEC were seeded in serum-free media in multiwell chamber slides on complete Matrigel, allowed to adhere for 1 hr after which another layer of complete Matrigel was uniformly pipetted on top of the adherent cells. After another hour of incubation, different treatments were added to the media: either VCN (100 and 1000 nM), the cRGDfV peptide (1 and 10 µM), Avastin (100 nM), the 7E3 F(ab')2 antibody fragment (100 nM) or the anti-αvβ3 monoclonal antibody LM609 (100 nM). Staurosporine (STSP), a known HUVEC apoptosis inducer and actin modifier, was used as a positive control at two different concentrations (100 and 1000 nM). The cells were then incubated for 16 hr at 37° C. in the presence of 5% $CO_2$. At the end of the incubation period, the cells from all conditions were fixed in 4% formaldehyde, permeabilized in 0.2% Triton X-100, FITC-TUNEL stained, and counterstained with Rhodamine-Phalloidin and Hoechst 33342. The amount of cell death was plotted for each condition by counting the apoptosis events from multiple random fields using the formula 'number of apoptotic nuclei/total number of nuclei×100'. The data shown above was generated from four independent experiments.

FIG. 10 shows that VCN is an efficient inducer of apoptosis in tubulogenic HUVEC seeded between two Matrigel layers.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such tennis and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

All publications, patent applications, patents, and other references mentioned herein are expressly incorporated by reference in their entirety, including all formulas and figures, to the same extent as if each were incorporated by reference individually. In case of conflict, the present specification, including definitions, will control.

Other embodiments are set forth within the following claims.

REFERENCES

Abercrombie, M., Heaysman, J. E., and Pegrum, S. M. (1970) "The locomotion of fibroblasts in culture. 3. Movements of particles on the dorsal surface of the leading lamella." *Exp Cell Res* 62: 389-398.
Albrecht-Buehler, G. (1977) "The phagokinetic tracks of 3T3 cells." *Cell* 11: 395-404.
Bessette, P. H., F. Aslund, et al. (1999). "Efficient folding of proteins with multiple disulfide bonds in the *Escherichia coli* cytoplasm." *Proc Natl Acad Sci USA* 96(24): 13703-8.
Bessette, P. H., J. Qiu, et al. (2001). "Effect of sequences of the active-site dipeptides of DsbA and DsbC on in vivo folding of multidisulfide proteins in *Escherichia coli*." *J Bacteriol* 183(3): 980-8.
Bilgrami, S., S. Tomar, et al. (2004). "Crystal structure of schistatin, a disintegrin homodimer from saw-scaled viper (*Echis carinatus*) at 2.5 A resolution." *J Mol Biol* 341(3): 829-37.

Bowersox, J. C. and Sorgente, N. (1982) "Chemotaxis of aortic endothelial cells in response to fibronectin." *Cancer Res* 42: 2547-2551.

Calvete, J. J., M. Jurgens, et al. (2000). "Disulphide-bond pattern and molecular modelling of the dimeric disintegrin EMF-10, a potent and selective integrin alpha5beta1 antagonist from Eristocophis macmahoni venom." *Biochem J* 345 Pt 3: 573-81.

Collet, J. F. and J. C. Bardwell (2002). "Oxidative protein folding in bacteria." *Mol Microbiol* 44(1): 1-8.

Collet, J. F., J. Riemer, et al. (2002). "Reconstitution of a disulfide isomerization system." *J Biol Chem* 277(30): 26886-92.

Dubendorff, J. W. and F. W. Studier (1991). "Controlling basal expression in an inducible T7 expression system by blocking the target T7 promoter with lac repressor." *J Mol Biol* 219(1): 45-59.

Goldstone, D., P. W. Haebel, et al. (2001). "DsbC activation by the N-terminal domain of DsbD." *Proc Natl Acad Sci USA* 98(17): 9551-6.

Gould, R. J., M. A. Polokoff, et al. (1990). "Disintegrins: a family of integrin inhibitory proteins from viper venoms." *Proc Soc Exp Biol Med* 195(2): 168-71.

Goulding, C. W., M. R. Sawaya, et al. (2002). "Thiol-disulfide exchange in an immunoglobulin-like fold: structure of the N-terminal domain of DsbD." *Biochemistry* 41(22): 6920-7.

Jurado, P., D. Ritz, et al. (2002). "Production of functional single-chain Fv antibodies in the cytoplasm of *Escherichia coli*." *J Mol Biol* 320(1): 1-10.

LaVallie, E. R., E. A. DiBlasio, et al. (1993). "A thioredoxin gene fusion expression system that circumvents inclusion body formation in the *E. coli* cytoplasm." *Biotechnology* (N Y) 11(2): 187-93.

Levy, R., R. Weiss, et al. (2001). "Production of correctly folded Fab antibody fragment in the cytoplasm of *Escherichia coli* trxB gor mutants via the coexpression of molecular chaperones." *Protein Expr Purif* 23(2): 338-47.

Markland, F. S., K. Shieh, et al. (2001). "A novel snake venom disintegrin that inhibits human ovarian cancer dissemination and angiogenesis in an orthotopic nude mouse model." *Haemostasis* 31(3-6): 183-91.

Martin, J. L. (1995). "Thioredoxin—a fold for all reasons." *Structure* 3(3): 245-50.

Maskos, K., M. Huber-Wunderlich, et al. (2003). "DsbA and DsbC-catalyzed oxidative folding of proteins with complex disulfide bridge patterns in vitro and in vivo." *J Mol Biol* 325(3): 495-513.

McLane, M. A., C. Marcinkiewicz, et al. (1998). "Viper venom disintegrins and related molecules." *Proc Soc Exp Biol Med* 219(2): 109-19.

Moiseeva, N., S. D. Swenson, et al. (2002). "Purification, crystallization and preliminary X-ray analysis of the disintegrin contortrostatin from Agkistrodon contortrix contortrix snake venom." *Acta Crystallogr D Biol Crystallogr* 58 (Pt 12): 2122-4.

Moiseeva, N., Bau, R., Swenson, S. D., Markland, F. S., Jun-YongC., Zhi-Jie, L. and Allaire, M. (2008) "Crystal structure of Acostatin, a dimeric disintegrin from Southern copperhead (Agkistrodon contortrix contortrix) at 1.7 Å resolution." *Acta Crystallographica* D64:466-470.

Mossner, E., M. Huber-Wunderlich, et al. (1998). "Characterization of *Escherichia coli* thioredoxin variants mimicking the active-sites of other thiol/disulfide oxidoreductases." *Protein Sci* 7(5): 1233-44.

Moura-da-Silva, A. M., A. Linica, et al. (1999). "Jararhagin ECD-containing disintegrin domain: expression in *escherichia coli* and inhibition of the platelet-collagen interaction." *Arch Biochem Biophys* 369(2): 295-301.

Niewiarowski, S., M. A. McLane, et al. (1994). "Disintegrins and other naturally occurring antagonists of platelet fibrinogen receptors." *Semin Hematol* 31(4): 289-300.

Park, S. H. and Raines, R. T. "Fluorescence polarization assay to quantify protein-protein interactions." *Methods Mol Biol* 261: 161-166, 2004

Prinz, W. A., F. Aslund, et al. (1997). "The role of the thioredoxin and glutaredoxin pathways in reducing protein disulfide bonds in the *Escherichia coli* cytoplasm." *J Biol Chem* 272(25): 15661-7.

Ritter, M. R., Zhou, Q., and Markland, F. S., Jr. (2000) Contortrostatin, a snake venom disintegrin, induces alphavbeta3-mediated tyrosine phosphorylation of CAS and FAK in tumor cells. *J Cell Biochem* 79: 28-37.

Savage, B., U. M. Marzec, et al. (1990). "Binding of the snake venom-derived proteins applaggin and echistatin to the arginine-glycine-aspartic acid recognition site(s) on platelet glycoprotein IIb.IIIa complex inhibits receptor function." *J Biol Chem* 265(20): 11766-72.

Scarborough, R. M., J. W. Rose, et al. (1991). "Barbourin. A GPIIb-IIIa-specific integrin antagonist from the venom of Sistrurus m. barbouri." *J Biol Chem* 266(15): 9359-62.

Schmitmeier, S., F. S. Markland, et al. (2000). "Anti-invasive effect of contortrostatin, a snake venom disintegrin, and TNF-alpha on malignant glioma cells." *Anticancer Res* 20(6B): 4227-33.

Schmitmeier, S., Markland, F. S., Schonthal, A. H., and Chen, T. C. (2005) "Potent mimicry of fibronectin-induced intracellular signaling in glioma cells by the homodimeric snake venom disintegrin contortrostatin." *Neurosurgery* 57: 141-153; discussion 141-153.

Stewart, E. J., F. Aslund, et al. (1998). "Disulfide bond formation in the *Escherichia coli* cytoplasm: an in vivo role reversal for the thioredoxins." *Embo J* 17(19): 5543-50.

Studier, F. W. (1991), "Use of bacteriophage T7 lysozyme to improve an inducible T7 expression system." *J Mol Biol* 219(1): 37-44.

Studier, F. W., A. H. Rosenberg, et al. (1990). "Use of T7 RNA polymerase to direct expression of cloned genes." *Methods Enzymol* 185: 60-89.

Swenson, S., F. Costa, et al. (2004). "Intravenous liposomal delivery of the snake venom disintegrin contortrostatin limits breast cancer progression." *Mol Cancer Ther* 3(4): 499-511.

Trikha, M., Y. A. De Clerck, et al. (1994). "Contortrostatin, a snake venom disintegrin, inhibits beta 1 integrin-mediated human metastatic melanoma cell adhesion and blocks experimental metastasis." *Cancer Res* 54(18): 4993-8.

Trikha, M., W. E. Rote, et al. (1994). "Purification and characterization of platelet aggregation inhibitors from snake venoms." *Thromb Res* 73(1): 39-52.

Venturi, M., C. Seifert, et al. (2002). "High level production of functional antibody Fab fragments in an oxidizing bacterial cytoplasm." *J Mol Biol* 315(1): 1-8.

Zetter, B. R. (1980) "Migration of capillary endothelial cells is stimulated by tumour-derived factors." *Nature* 285: 41-43.

Zhou, Q., P. Hu, et al. (2000). "Molecular cloning and functional expression of contortrostatin, a homodimeric disintegrin from southern copperhead snake venom." *Arch Biochem Biophys* 375(2): 278-88.

Zhou, Q., M. T. Nakada, et al. (1999). "Contortrostatin, a dimeric disintegrin from Agkistrodon contortrix contortrix, inhibits angiogenesis." *Angiogenesis* 3(3): 259-69.

Zhou, Q., M. T. Nakada, et al. (2000). "Contortrostatin, a homodimeric disintegrin, binds to integrin alphavbeta5." *Biochem Biophys Res Commun* 267(1): 350-5.

Zhou, Q., R. P. Sherwin, et al. (2000). "Contortrostatin, a dimeric disintegrin from Agkistrodon contortrix contortrix, inhibits breast cancer progression." *Breast Cancer Res Treat* 61(3): 249-60.

That which is claimed is:

1. A method of expressing non-procaryotic biologically active disulfide-rich protein in prokaryotic host cells said method comprising the steps:
   a) obtaining a prokaryotic host cell transformed with an expression vector encoding a fusion protein under inducible control, said fusion protein comprising an N-terminal segment encoding thioredoxin and a C-terminal segment encoding said disulfide rich protein, wherein said host also carries stable mutations in thioredoxin reductase B (trxB) gene and/or the glutathione reductase (gor) gene, wherein said expression vector has an antibiotic resistance gene which makes it selectable on a first antibiotic, and wherein said trxB and gor mutations are selectable on at least one additional antibiotic to maintain the expression vector and trxB and gor mutations in said host cells during growth;
   b) growing the host cells of step a) in the presence of the first and said at least one additional antibiotic to obtain a sufficient number of cells suitable to seed a reactor in which host cells will be grown and the fusion protein expression induced; and
   c) seeding the reactor with the cells of step b) and growing the cells and inducing expression of the fusion protein, wherein said cells in the reactor are grown in the presence of the first antibiotic and in the absence of said at least one additional antibiotic.

2. The method of claim 1 wherein the host cells express mutant products of both the trxB and gor genes.

3. The method of claim 1 wherein said host cells are mutant in both trxB and gor genes.

4. The method of claim 3 wherein the trxB and gor genes are selectable on different antibiotics.

5. The method of claim 1 wherein the thioredoxin portion of the fusion protein comprises SEQ ID NO: 1.

6. The method of claim 1 wherein the host is deficient in any one or more of ompT or lon gene products.

7. The method of claim 1 wherein a sequence encoding a cleavage site is located between the sequence encoding thioredoxin and the sequence encoding the disulfide rich protein.

8. The method of claim 1 wherein the fusion protein further comprises a peptide sequence which is a ligand for a receptor.

9. The method of claim 1 wherein the reactor comprises a fermentation vessel.

10. The method of claim 1 wherein the prokaryotic host cell comprises a bacterial host cell.

11. The method of claim 1 wherein said bacterial host cell comprises an Origami strain or Rosetta-gami strain.

12. The method of claim 1, further comprising a step following step c, wherein the cells are harvested and processed to obtain a purified preparation of said biologically active disulfide rich protein.

13. The method of claim 1 wherein said biologically active disulfide rich protein is Vicrostatin (VCN), comprising the amino acid sequence of SEQ ID NO: 3.

14. The method of claim 13 wherein said VCN is expressed as a monomer.

15. The method of claim 12, wherein said biologically active disulfide rich protein is Vicrostatin (VCN) comprising the amino acid sequence of SEQ ID NO: 3 and which is at least 50% pure.

16. The method of claim 12, wherein said biologically active disulfide rich protein is Vicrostatin (VCN) comprising the amino acid sequence of SEQ ID NO: 3 and which is at least 90% pure.

17. The method of claim 12, wherein said biologically active disulfide rich protein is Vicrostatin (VCN) comprising the amino acid sequence of SEQ ID NO: 3 and which is at least 99% pure.

18. The method of claim 13 wherein said biologically active VCN inhibits the migration of HUVEC, MDA-MB-435 or MDA-MB-231 cells.

19. The method of claim 13 wherein said biologically active VCN increases the level of phosphorylation of FAK in MDA-MB-435 cells.

20. The method of claim 13 wherein said biologically active VCN induces apoptosis in HUVECs in culture.

21. The method of claim 3 wherein said biologically active VCN inhibits tube formation of HUVECs in culture.

* * * * *

```
                          SEQUENCE LISTING

<160> NUMBER OF SEQ ID NOS: 22

<210> SEQ ID NO 1
   <211> LENGTH: 109
   <212> TYPE: PRT
   <213> ORGANISM: Escherichia coli

<400> SEQUENCE: 1

Met Ser Asp Lys Ile Ile His Leu Thr Asp Asp Ser Phe Asp Thr Asp
   1               5                   10                  15

Val Leu Lys Ala Asp Gly Ala Ile Leu Val Asp Phe Trp Ala Glu Trp
                   20                  25                  30

Cys Gly Pro Cys Lys Met Ile Ala Pro Ile Leu Asp Glu Ile Ala Asp
                   35                  40                  45

Glu Tyr Gln Gly Lys Leu Thr Val Ala Lys Leu Asn Ile Asp Gln Asn
           50                  55                  60

Pro Gly Thr Ala Pro Lys Tyr Gly Ile Arg Gly Ile Pro Thr Leu Leu
   65                  70                  75                  80

Leu Phe Lys Asn Gly Glu Val Ala Ala Thr Lys Val Gly Ala Leu Ser
                   85                  90                  95

Lys Gly Gln Leu Lys Glu Phe Leu Asp Ala Asn Leu Ala
                   100                 105

<210> SEQ ID NO 2
   <211> LENGTH: 64
   <212> TYPE: PRT
   <213> ORGANISM: Agkistrodon contortrix

<400> SEQUENCE: 2

Asp Ala Pro Ala Asn Pro Cys Cys Asp Ala Ala Thr Cys Lys Leu Thr
   1               5                   10                  15

Thr Gly Ser Gln Cys Ala Asp Gly Leu Cys Cys Asp Gln Cys Lys Phe
                   20                  25                  30

Met Lys Glu Gly Thr Val Cys Arg Arg Ala Arg Gly Asp Asp Leu Asp
                   35                  40                  45

Asp Tyr Cys Asn Gly Ile Ser Ala Gly Cys Pro Arg Asn Pro Phe His
           50                  55                  60

<210> SEQ ID NO 3
   <211> LENGTH: 70
   <212> TYPE: PRT
   <213> ORGANISM: Artificial Sequence
   <220> FEATURE:
   <223> OTHER INFORMATION: Description of Artificial Sequence: Synthetic
         polypeptide

<400> SEQUENCE: 3

Asp Ala Pro Ala Asn Pro Cys Cys Asp Ala Ala Thr Cys Lys Leu Thr
   1               5                   10                  15

Thr Gly Ser Gln Cys Ala Asp Gly Leu Cys Cys Asp Gln Cys Lys Phe
                   20                  25                  30
```

```
Met Lys Glu Gly Thr Val Cys Arg Ala Arg Gly Asp Leu Asp
         35                  40                  45
Asp Tyr Cys Asn Gly Ile Ser Ala Gly Cys Pro Arg Asn Pro Phe His
 50                  55                  60
His Lys Gly Pro Ala Thr
 65                  70

<210> SEQ ID NO 4
<211> LENGTH: 217
<212> TYPE: PRT
<213> ORGANISM: Escherichia coli
<220> FEATURE:
<221> NAME/KEY: MOD_RES
<222> LOCATION: (207)..(207)
<223> OTHER INFORMATION: Any amino acid

<400> SEQUENCE: 4

Asp Asp Ala Ala Ile Gln Gln Thr Leu Ala Lys Met Gly Ile Lys Ser
 1               5                  10                  15
Ser Asp Ile Gln Pro Ala Pro Val Ala Gly Met Lys Thr Val Leu Thr
                20                  25                  30
Asn Ser Gly Val Leu Tyr Ile Thr Asp Asp Gly Lys His Ile Ile Gln
         35                  40                  45
Gly Pro Met Tyr Asp Val Ser Gly Thr Ala Pro Val Cys Asn Val Thr
 50                  55                  60
Asn Lys Met Leu Leu Lys Gln Leu Asn Ala Leu Glu Lys Glu Met Ile
 65                  70                  75                  80
Val Tyr Lys Ala Pro Gln Glu Lys His Val Ile Thr Val Phe Thr Asp
                 85                  90                  95
Ile Thr Cys Gly Tyr Cys His Lys Leu His Glu Gln Met Ala Asp Tyr
                100                 105                 110
Asn Ala Leu Gly Ile Thr Val Arg Tyr Leu Ala Phe Pro Arg Gln Gly
            115                 120                 125
Leu Asp Ser Asp Ala Glu Lys Glu Met Lys Ala Ile Trp Cys Ala Lys
        130                 135                 140
Asp Lys Asn Lys Ala Phe Asp Asp Val Met Ala Gly Lys Ser Val Ala
145                 150                 155                 160
Pro Ala Ser Cys Asp Val Asp Ile Ala Asp His Tyr Ala Leu Gly Val
                165                 170                 175
Gln Leu Gly Val Ser Gly Thr Pro Ala Val Val Leu Ser Asn Gly Thr
            180                 185                 190
Leu Val Pro Gly Tyr Gln Pro Pro Lys Glu Met Lys Glu Phe Xaa Asp
        195                 200                 205
Glu His Gln Lys Met Thr Ser Gly Lys
    210                 215

<210> SEQ ID NO 5
<211> LENGTH: 132
<212> TYPE: PRT
<213> ORGANISM: Escherichia coli

<400> SEQUENCE: 5

Gly Leu Phe Asp Ala Pro Gly Arg Ser Gln Phe Val Pro Ala Asp Gln
 1               5                  10                  15
Ala Phe Ala Phe Asp Phe Gln Gln Asn Gln His Asp Leu Asn Leu Thr
                20                  25                  30
Trp Gln Ile Lys Asp Gly Tyr Tyr Leu Tyr Arg Lys Gly Ile Arg Ile
         35                  40                  45
```

```
Thr Pro Glu His Ala Lys Ile Ala Asp Val Gln Leu Pro Gln Gly Val
        50                  55                  60

Trp His Glu Asp Glu Phe Tyr Gly Lys Ser Glu Ile Tyr Arg Asp Arg
 65                  70                  75                  80

Leu Thr Leu Pro Val Thr Ile Asn Gln Ala Ser Ala Gly Ala Thr Leu
                 85                  90                  95

Thr Val Thr Tyr Gln Gly Cys Ala Asp Ala Gly Phe Cys Tyr Pro Pro
                100                 105                 110

Glu Thr Lys Thr Val Pro Leu Ser Glu Val Val Ala Asn Asn Glu Ala
            115                 120                 125

Ser Gln Pro Val
    130

<210> SEQ ID NO 6
<211> LENGTH: 4
<212> TYPE: PRT
<213> ORGANISM: Escherichia coli

<400> SEQUENCE: 6

Cys Gly Pro Cys
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Pro Tyr Cys
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Gly His Cys
1

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

His Lys Gly Pro Ala Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (7)..(7)
<223> OTHER INFORMATION: Gly or Ser

<400> SEQUENCE: 10

Glu Asn Leu Tyr Phe Gln Xaa
1               5

<210> SEQ ID NO 11
<211> LENGTH: 4
<212> TYPE: PRT
<213> ORGANISM: Escherichia coli

<400> SEQUENCE: 11

Cys Gly Tyr Cys
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Gly Phe Cys
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Thr Phe Cys
1

<210> SEQ ID NO 14
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gttccagatc tcgagaatct ttacttccaa ggagacgctc tgcaaatcc gtgctgcga      59

<210> SEQ ID NO 15
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gttattcgcc atggcttaag tagctggacc cttgtgggga tttctgggac agccagcaga    60
tatgcc                                                               66
```

```
<210> SEQ ID NO 16
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ala Pro Ala Asn Pro Cys Cys Asp Ala Ala Thr Cys Lys Leu Thr
1               5                   10                  15

Thr Gly Ser Gln Cys Ala Asp Gly Leu Cys Cys Asp Gln Cys Lys Phe
            20                  25                  30

Met Lys Glu Gly Thr Val Cys Arg Arg Ala Arg Gly Asp Asp Leu Asp
        35                  40                  45

Asp Tyr Cys Asn Gly Ile Ser Ala Gly Cys Pro Arg Asn Pro Phe His
    50                  55                  60

Ala
65

<210> SEQ ID NO 17
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ala Pro Ala Asn Pro Cys Cys Asp Ala Ala Thr Cys Lys Leu Thr
1               5                   10                  15

Thr Gly Ser Gln Cys Ala Asp Gly Leu Cys Cys Asp Gln Cys Lys Phe
            20                  25                  30

Met Lys Glu Gly Thr Val Cys Arg Arg Ala Arg Gly Asp Asp Leu Asp
        35                  40                  45

Asp Tyr Cys Asn Gly Ile Ser Ala Gly Cys Pro Arg Asn Pro Phe His
    50                  55                  60

Ala
65

<210> SEQ ID NO 18
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gly Asp Ala Pro Ala Asn Pro Cys Cys Asp Ala Ala Thr Cys Lys Leu
1               5                   10                  15

Thr Thr Gly Ser Gln Cys Ala Asp Gly Leu Cys Cys Asp Gln Cys Lys
            20                  25                  30

Phe Met Lys Glu Gly Thr Val Cys Arg Arg Ala Arg Gly Asp Asp Leu
        35                  40                  45

Asp Asp Tyr Cys Asn Gly Ile Ser Ala Gly Cys Pro Arg Asn Pro His
    50                  55                  60

Lys Gly Pro Ala Thr
65

<210> SEQ ID NO 19
```

<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Cys Glu Ser Gly Pro Cys Cys Arg Asn Cys Lys Phe Leu Lys Glu
1               5                   10                  15

Gly Thr Ile Cys Lys Arg Ala Arg Gly Asp Asp Met Asp Asp Tyr Cys
            20                  25                  30

Asn Gly Lys Thr Cys Asp Cys Pro Arg Asn Pro His Lys Gly Pro Ala
        35                  40                  45

Thr

<210> SEQ ID NO 20
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ala Pro Ala Asn Pro Cys Cys Asp Ala Ala Thr Cys Lys Leu Thr
1               5                   10                  15

Thr Gly Ser Gln Cys Ala Asp Gly Leu Cys Cys Asp Gln Cys Lys Phe
            20                  25                  30

Met Lys Glu Gly Thr Val Cys Arg Arg Ala Arg Gly Asp Asp Leu Asp
            35                  40                  45

Asp Tyr Cys Asn Gly Ile Ser Ala Gly Cys Pro Arg Asn Pro Phe His
        50                  55                  60

<210> SEQ ID NO 21
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Cys Glu Ser Gly Pro Cys Cys Arg Asn Cys Lys Phe Leu Lys Glu
1               5                   10                  15

Gly Thr Ile Cys Lys Arg Ala Arg Gly Asp Asp Met Asp Asp Tyr Cys
            20                  25                  30

Asn Gly Lys Thr Cys Asp Cys Pro Arg Asn Pro His Lys Gly Pro Ala
        35                  40                  45

Thr

<210> SEQ ID NO 22
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ala Pro Ala Asn Pro Cys Cys Asp Ala Ala Thr Cys Lys Leu Thr
1               5                   10                  15

```
Thr Gly Ser Gln Cys Ala Asp Gly Leu Cys Cys Asp Gln Cys Lys Phe
            20                  25                  30

Met Lys Glu Gly Thr Val Cys Arg Arg Ala Arg Gly Asp Asp Leu Asp
        35                  40                  45

Asp Tyr Cys Asn Gly Ile Ser Ala Gly Cys Pro Arg Asn Pro His Lys
        50                  55                  60

Gly Pro Ala Thr
65
```